(12) United States Patent
Kamatani et al.

(10) Patent No.: US 8,822,043 B2
(45) Date of Patent: Sep. 2, 2014

(54) ORGANIC COMPOUND AND ORGANIC LIGHT-EMITTING DEVICE

(75) Inventors: Jun Kamatani, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 252 days.

(21) Appl. No.: 13/379,951

(22) PCT Filed: Apr. 27, 2010

(86) PCT No.: PCT/JP2010/057841
§ 371 (c)(1),
(2), (4) Date: Dec. 21, 2011

(87) PCT Pub. No.: WO2011/001741
PCT Pub. Date: Jan. 6, 2011

(65) Prior Publication Data
US 2012/0091450 A1    Apr. 19, 2012

(30) Foreign Application Priority Data
Jun. 30, 2009   (JP) .................................. 2009-155667

(51) Int. Cl.
| | | |
|---|---|---|
| H01L 51/54 | (2006.01) | |
| C07C 13/62 | (2006.01) | |
| C07D 213/16 | (2006.01) | |
| C07D 251/24 | (2006.01) | |
| C07C 13/70 | (2006.01) | |
| H01L 27/146 | (2006.01) | |
| C07C 211/61 | (2006.01) | |
| H01L 51/50 | (2006.01) | |
| C07D 215/04 | (2006.01) | |
| C07D 235/18 | (2006.01) | |
| C07D 403/10 | (2006.01) | |
| H05B 33/14 | (2006.01) | |
| H01L 51/00 | (2006.01) | |
| C07D 333/08 | (2006.01) | |
| C09K 11/06 | (2006.01) | |
| C07D 401/10 | (2006.01) | |

(52) U.S. Cl.
CPC ............ *C09K 11/06* (2013.01); *H01L 51/5016* (2013.01); *C07C 2103/18* (2013.01); *C07C 2103/24* (2013.01); *C07C 2103/54* (2013.01); *C07D 215/04* (2013.01); *C07D 235/18* (2013.01); *C07D 213/16* (2013.01); *C07D 251/24* (2013.01); *C07C 2103/40* (2013.01); *C09K 2211/1029* (2013.01); *C07C 211/61* (2013.01); *C07D 403/10* (2013.01); *H05B 33/14* (2013.01); *C07C 2101/14* (2013.01); *H01L 51/0056* (2013.01); *C07C 2103/26* (2013.01); *C07D 333/08* (2013.01); *C09K 2211/1011* (2013.01); *C07C 2103/50* (2013.01); *C07D 401/10* (2013.01); *C07C 13/62* (2013.01); *C09K 2211/1014* (2013.01); *C07C 2103/52* (2013.01); *Y10S 428/917* (2013.01)
USPC ........... 428/690; 428/917; 313/504; 313/506; 257/40; 546/285; 564/426; 544/180; 585/27

(58) Field of Classification Search
None
See application file for complete search history.

(56) References Cited

U.S. PATENT DOCUMENTS

| | | | | |
|---|---|---|---|---|
| 8,507,900 B2 * | 8/2013 | Mizuki | ........................... | 257/40 |
| 2002/0168544 A1 * | 11/2002 | Fukuoka et al. | .............. | 428/690 |
| 2003/0137241 A1 | 7/2003 | Fujita | | |
| 2003/0224202 A1 | 12/2003 | Brown | | |
| 2004/0076853 A1 * | 4/2004 | Jarikov | ........................ | 428/690 |

FOREIGN PATENT DOCUMENTS

| | | |
|---|---|---|
| EP | 1357613 A2 | 10/2003 |
| JP | 9-241629 A1 | 9/1997 |
| JP | 2005-068087 A | 3/2005 |
| JP | 4059822 B2 | 3/2008 |
| WO | 2008/059713 A1 | 5/2008 |
| WO | 2008/102740 A1 | 8/2008 |
| WO | 2009/008348 A | 1/2009 |
| WO | 2009/008359 A | 1/2009 |

* cited by examiner

*Primary Examiner* — Dawn Garrett
(74) *Attorney, Agent, or Firm* — Canon U.S.A., Inc., IP Division

(57) ABSTRACT

The present invention provides organic compounds which are indenobenzo[k]fluoranthene derivatives represented by the following general formula (1):

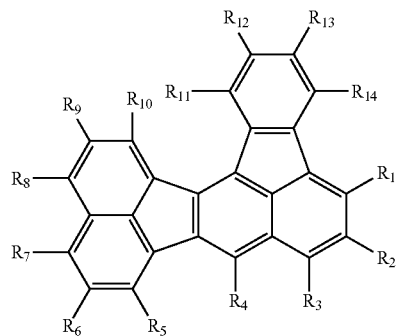

In general formula (1), $R_1$ to $R_{14}$ are each independently selected from a hydrogen atom, a halogen atom, an alkyl group, an alkoxy group, an amino group, an aryl group, and a heterocyclic group.

10 Claims, 1 Drawing Sheet

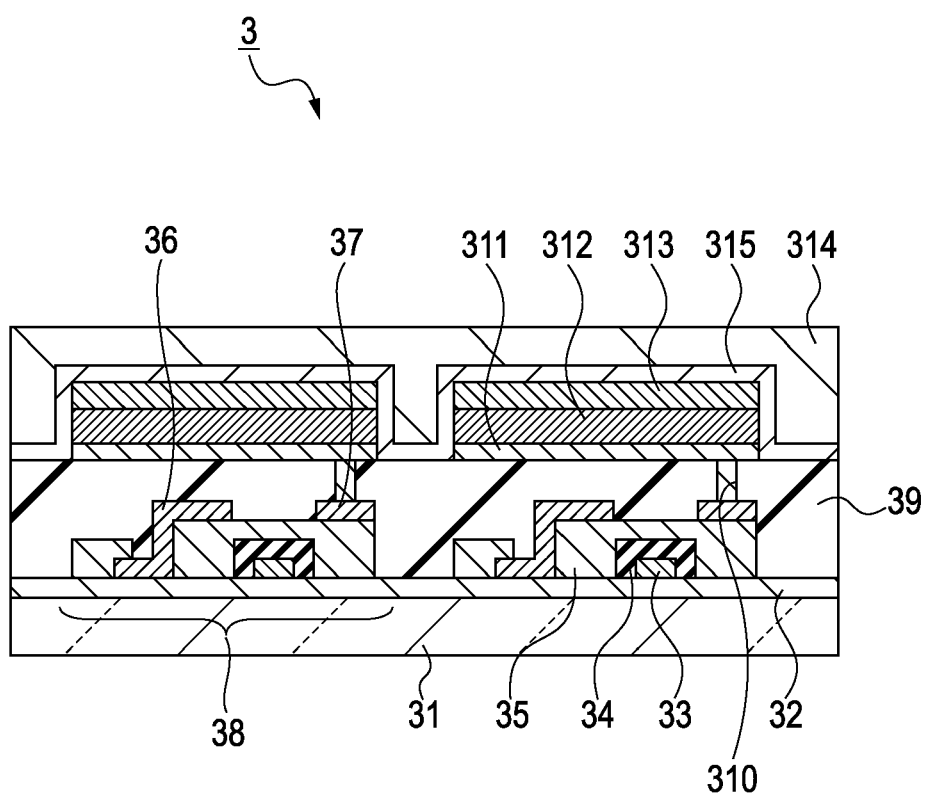

ORGANIC COMPOUND AND ORGANIC LIGHT-EMITTING DEVICE

TECHNICAL FIELD

The present invention relates to novel organic compounds and an organic light-emitting device and an image display device including the compounds.

BACKGROUND ART

Organic light-emitting devices are devices each including an anode, a cathode, and an organic compound layer disposed between the two electrodes. Electrons and holes are injected from the electrodes to generate excitons of a luminescent organic compound in the organic compound layer, and light is emitted when the excitons return to the ground state.

The organic light-emitting devices are referred to as "organic electroluminescence devices" or "organic EL devices".

In recent years, remarkable progress has been made in the organic light-emitting devices to permit the formation of thin and lightweight light-emitting devices having high luminance at low applied voltage, diversity in emission wavelengths, and rapid response.

The organic light-emitting devices can be used as exposure light sources for exposing photosensitive members of image display devices and electrophotographic image forming apparatuses.

Novel luminescent organic compounds have been created so far.

For example, PTL 1 discloses IK-12 shown below as an example of an organic compound constituting a light-emitting layer serving as an organic compound layer. This compound has, as a basic skeleton, benzo[k]fluoranthene shown below. The basic skeleton represents a condensed ring having a conjugated ring structure.

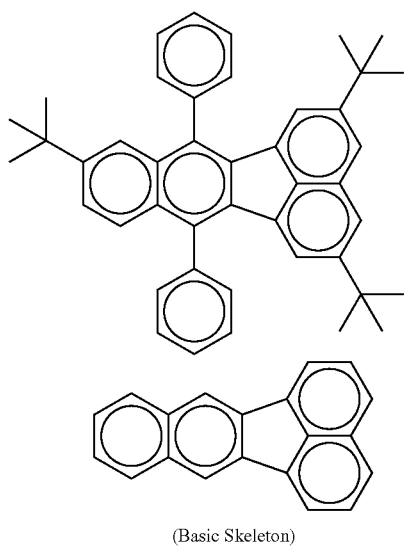

(IK-12)

(Basic Skeleton)

CITATION LIST

Patent Literature

PTL 1 Japanese Patent Laid-Open No. 9-241629 (no corresponding foreign application)

SUMMARY OF INVENTION

The benzo[k]fluoranthene can emit light only in the ultraviolet region but not blue light. IK-12 emits blue light when the basic skeleton is provided with a substituent.

The present invention provides novel organic compounds having a basic skeleton capable of emitting light in a blue region.

Accordingly, the present invention provides organic compounds represented by the following general formula (1).

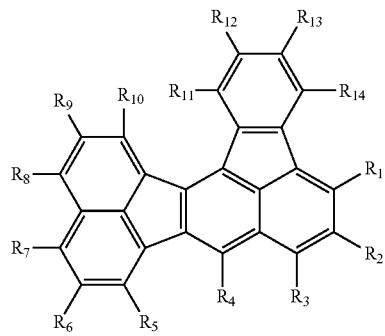

General Formula (1)

In the general formula (1), $R_1$ to $R_{14}$ are each independently selected from a hydrogen atom, a halogen atom, an alkyl group, an alkoxy group, an amino group, an aryl group, and a heterocyclic group.

The present invention can provide novel organic compounds having a basic skeleton with a wide band gap and a deep LUMO (Lowest Unoccupied Molecular Orbital). The organic compounds according to the present invention have a basic skeleton capable of emitting light in the blue region. It is also possible to provide novel organic compounds capable of emitting not only blue light but also green light and red light when a substituent is introduced into a basic skeleton. Further, an organic light-emitting device including any one of these novel organic compounds can be provided.

BRIEF DESCRIPTION OF DRAWINGS

FIG. 1 is a schematic sectional view showing an organic light-emitting device and TFT (Thin Film Transistor) connected to the organic light-emitting device.

DESCRIPTION OF EMBODIMENTS

First, organic compounds according to the present invention are described.

The organic compounds according to the present invention are indenobenzo[k]fluoranthene derivatives represented by the following general formula (1).

General Formula (1)

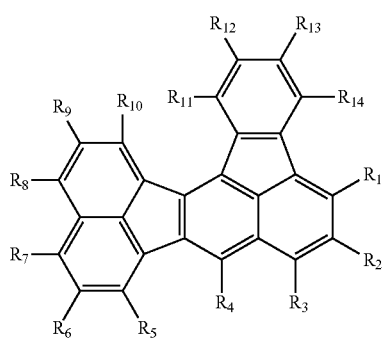

In the general formula (1), $R_1$ to $R_{14}$ are each independently selected from a hydrogen atom, a halogen atom, an alkyl group, an alkoxy group, an amino group, an aryl group, and a heterocyclic group.

Herein, an alkyl group may have a substituent. Examples of the substituent which may be possessed by the alkyl group include alkyl groups, such as a methyl group, an ethyl group, a propyl group, and the like; aralkyl groups, such as a benzyl group and the like; aryl groups, such as a phenyl group, a biphenyl group, and the like; heterocyclic groups, such as a pyridyl group, a pyrrolyl group, and the like; amino groups, such as a dimethylamino group, a diethylamino group, a diphenylamino group, a ditolylamino group, and the like; alkoxyl groups, such as a methoxyl group, a phenoxyl group, and the like; a cyano group; and halogen atoms, such as fluorine, chlorine, bromine, iodine, and the like. Of course, the substituent is not limited to these groups.

An alkoxy group may have a substituent. Examples of the substituent which may be possessed by the alkoxy group include alkyl groups, such as a methyl group, an ethyl group, a propyl group, and the like; aralkyl groups, such as a benzyl group and the like; aryl groups, such as a phenyl group, a biphenyl group, and the like; heterocyclic groups, such as a pyridyl group, a pyrrolyl group, and the like; amino groups, such as a dimethylamino group, a diethylamino group, a diphenylamino group, a ditolylamino group, and the like; alkoxyl groups, such as a methoxyl group, a phenoxyl group, and the like; a cyano group; and halogen atoms, such as fluorine, chlorine, bromine, iodine, and the like. Of course, the substituent is not limited to these groups.

An amino group may have a substituent. Examples of the substituent which may be possessed by the amino group include alkyl groups, such as a methyl group, an ethyl group, a propyl group, and the like; aralkyl groups, such as a benzyl group and the like; aryl groups, such as a phenyl group, a biphenyl group, and the like; heterocyclic groups, such as a pyridyl group, a pyrrolyl group, and the like; amino groups, such as a dimethylamino group, a diethylamino group, a diphenylamino group, a ditolylamino group, and the like; alkoxyl groups, such as a methoxyl group, a phenoxyl group, and the like; a cyano group; and halogen atoms, such as fluorine, chlorine, bromine, iodine, and the like. Of course, the substituent is not limited to these groups.

An aryl group may have a substituent. Examples of the substituent which may be possessed by the aryl group include alkyl groups, such as a methyl group, an ethyl group, a propyl group, and the like; aralkyl groups, such as a benzyl group and the like; aryl groups, such as a phenyl group, a biphenyl group, and the like; heterocyclic groups, such as a pyridyl group, a pyrrolyl group, and the like; amino groups, such as a dimethylamino group, a diethylamino group, a diphenylamino group, a ditolylamino group, and the like; alkoxyl groups, such as a methoxyl group, a phenoxyl group, and the like; a cyano group; and halogen atoms, such as fluorine, chlorine, bromine, iodine, and the like. Of course, the substituent is not limited to these groups.

A heterocyclic group may have a substituent. Examples of the substituent which may be possessed by the heterocyclic group include alkyl groups, such as a methyl group, an ethyl group, a propyl group, and the like; aralkyl groups, such as a benzyl group and the like; aryl groups, such as a phenyl group, a biphenyl group, and the like; heterocyclic groups, such as a pyridyl group, a pyrrolyl group, and the like; amino groups, such as a dimethylamino group, a diethylamino group, a diphenylamino group, a ditolylamino group, and the like; alkoxyl groups, such as a methoxyl group, a phenoxyl group, and the like; a cyano group; and halogen atoms, such as fluorine, chlorine, bromine, iodine, and the like. Of course, the substituent is not limited to these groups.

The same applies to R shown in general formulae (2) and (3) described below.

The inventors of the present invention paid attention to the basic skeleton itself. Specifically, the inventors attempted to provide organic compounds having a basic skeleton whose molecules have an emission wavelength within a desired emission wavelength region.

Although it is known that a substituent is provided on the basis skeleton in order to obtain a desired emission wavelength, stability of compounds may be impaired.

In the present invention, the desired emission wavelength region is a blue region, specifically 430 nm or more and 480 nm or less.

(Comparison Between indenobenzo[k]fluoranthene Derivatives and Other Organic Compounds)

Organic compounds having benzo[k]fluoranthene are compared with organic compounds having indenobenzo[k]fluoranthene according to the present invention.

7,12-diphenylbenzo[k]fluoranthene as a comparison object is represented by the following structural formula:

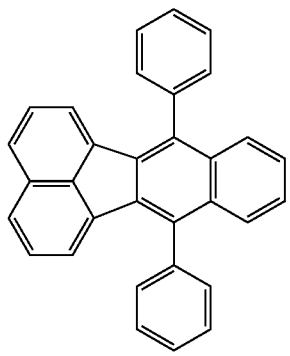 [SMILES: c1ccc(-c2c3c(c(-c4ccccc4)c4ccccc24)-c2cccc4cccc-3c24)cc1]

In addition, an indenobenzo[k]fluoranthene phenyl substitution product as an organic compound according to the present invention is represented by the following structural formula:

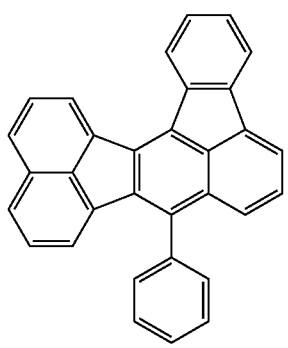 [SMILES: c1ccc(-c2c3cccc4c5ccccc5c(c34)c3c4cccc5cccc(c23)c54)cc1]

An organic compound having phenyl-substituted indenobenzo[k]fluoranthene, which is an organic compound according to the present invention, has the maximum emission wavelength of 443 nm. On the other hand, 7,12-diphenylbenzo[k]fluoranthene having benzo[k]fluoranthene substituted by phenyl groups at the 7- and 12-positions has the maximum emission wavelength of 428 nm. That is, in the organic compounds according to the present invention, the maximum emission wavelength lies in the blue light emission region within a range of 430 nm or more and 480 nm or less. On the other hand, the maximum emission wavelength of the organic compound as the comparison object deviates from the blue region to the shorter wavelength side. In addition, the calculated maximum emission wavelength of benzo[k]fluoranthene is 408 nm. Namely, the maximum emission wavelength of benzo[k]fluoranthene which is the basic skeleton falls in the ultraviolet region, but not the visible region.

This represents that the indenobenzo[k]fluoranthene skeleton according to the present invention emits light at the maximum emission wavelength of 430 nm or more and 480 nm or less. That is, the basic skeleton of the organic compounds according to the present invention can emit blue light by itself in the blue region within the range of 430 nm or more and 480 nm or less and a narrower range than this.

The basic skeleton of the organic compounds according to the present invention includes only a condensed ring structure, i.e., includes no rotational structure. Therefore, it is possible to suppress a reduction in quantum yield due to rotation and/or vibration.

In order to investigate conditions for the basic skeleton having the maximum emission wavelength within the blue light region, the inventors investigated the possibility of blue light emission of various skeletons having benzo[k]fluoranthene condensed with a 5-membered ring.

In the investigation, attention was paid to the four types of structural formulae shown in Table 1 below.

TABLE 1

| | Structural formula | Absorption wavelength (nm) | Predicted emission wavelength (nm) |
|---|---|---|---|
| a | | 378 | 408 |
| b | | 408 | 438 |
| c | | 464 | 494 |
| d | | 460 | 490 |

A structural formula shown by a in Table 1 represents benzo[k]fluoranthene. A structural formula shown by b in Table 1 represents indenobenzo[k]fluoranthene which is the basic skeleton possessed by the organic compounds according to the present invention. Structural formulae shown by c and d in Table 1 each represent a benzo[k]fluoranthene structure condensed with a 5-membered ring, which is a compound different from the indenobenzo[k]fluoranthene shown by b.

The calculated absorption wavelengths (S1) of the four types of compounds were determined by quantum chemical calculation. Changes of the maximum emission wavelength can be predicted by the absorption wavelengths. The predicted value of the emission wavelength was determined by adding 30 nm to the measured absorption wavelength. The results are shown in Table 1. The difference of 30 nm between the predicted emission wavelength and the absorption wavelength was determined from experience.

The maximum emission wavelengths of these structural formulae can be compared on the basis of the predicted emission wavelengths. This is because the predicted emission wavelength of 7,12-diphenylbenzo[k]fluoranthene as the comparison object is 420 nm, and, as described above, the measured value is 428 nm, so that the emission predicted value and the measured value can be considered to be substantially the same.

The absorption wavelengths shown in the table were determined by quantum chemical calculation on the B3LYP/6-31G* level using the density functional theory.

The four types of compounds shown in the table show different predicted emission wavelengths. The predicted emission wavelength of the first benzo[k]fluoranthene is 408 nm, i.e., out of the blue light emission region.

The predicted emission wavelengths of the compound c and the compound d shown in Table 1 are also out of the blue light emission region of 430 nm or more and 480 nm or less.

This represents that whether the skeleton has two 5-membered ring structures or the benzo[k]fluoranthene structure is condensed with a 5-membered ring, light in the blue light emission region cannot be emitted unless a 5-membered ring is provided in a specified position of the benzo[k]fluoranthene structure. That is, among these compounds, only the organic compound having as, the basic skeleton, indenobenzo[k]fluoranthene according to the present invention emits light in the blue light emission region by the basic skeleton alone.

Further, the organic compounds according to the present invention not only emit light in the blue light emission region by the basic skeleton alone but also have a low HOMO (Highest Occupied Molecular Orbital) energy level because of the two 5-membered ring structures provided in the basic skeleton. That is, the oxidation potential is low. In other words, the organic compounds according to the present invention are stable to oxidation.

Further, the organic compounds according to the present invention have no heteroatom such as nitrogen atom or the like in the basic skeleton. This also contributes to the low oxidation potential, i.e., contributes to oxidation stability of the organic compounds.

The basic skeleton of the organic compounds according to the present invention has a low HOMO energy level. That is, the LUMO level is also low.

The organic compound represented by IK-12 in CPL 1 has an electron-donating tertiary butyl group in order to perform blue light emission. Therefore, the organic compound has shallower HOMO and LUMO than those of benzo[k]fluoranthene. Namely, the organic compound represented by IK-12 has a high energy level and is thus susceptible to molecular oxidation. That is, the organic compounds according to the present invention are more stable to oxidation than the organic compound represented by IK-12.

The organic compounds according to the present invention are used as a guest material or host material of a light-emitting layer. Further, the organic compounds according to the present invention may be used for any layers other than the light-emitting layer, i.e., a hole injection layer, a hole transport layer, a hole/exciton blocking layer, an electron transport layer, and an electron injection layer.

The organic compounds according to the present invention can be used as a guest material of a light-emitting layer of an organic light-emitting device. In particular, the organic compounds according to the present invention can be used as a guest material of a blue light-emitting device.

The organic compounds according to the present invention can be used as a green luminescent material and red luminescent material by providing, on the basic skeleton, a substituent which can shift the emission wavelength to the longer wavelength side. The materials having longer emission wavelengths have the same basic skeleton as the organic compounds according to the present invention and are thus stable to oxidation.

Examples of the substituent which can shift the emission wavelength to the longer wavelength side include triarylamine, anthracene, and the like.

The organic compounds according to the present invention can be used as a guest material of a light-emitting layer, and a material having higher LUMO than the organic compounds, i.e., a material with an energy level closer to the vacuum level, can be used as a host material. This is because the organic compounds according to the present invention have a low LUMO and are thus capable of sufficiently receiving, from the host material, electrons which are supplied to the host material, i.e., a light-emitting layer.

The organic compounds according to the present invention have the basic skeleton with a wide band gap and thus can be used as host materials of green and red light-emitting layers.

With respect to the host material and the guest material, the host material is a compound having the highest weight ratio among the compounds constituting the light-emitting layer, and the guest material is a compound having a lower weight ratio than the host material among the compounds constituting the light-emitting layer.

The host material and the guest material are further described later. The organic compounds according to the present invention can be used as a guest material of a light-emitting layer of an organic light-emitting device. As a result, it is possible to provide organic light-emitting devices which emit blue light due to light emission from the organic compounds according to the present invention.

(Exemplification of Organic Compounds According to the Present Invention)

Examples of the compounds represented by the general formula (1) are given below. However, the present invention is not limited to these.

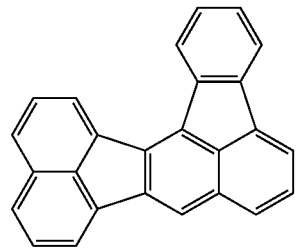

A1

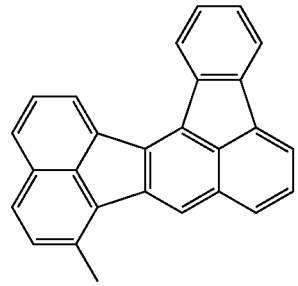

A2

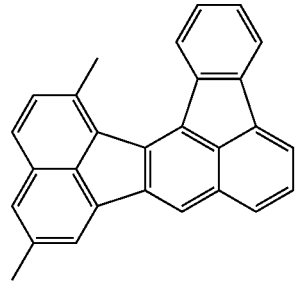

A3

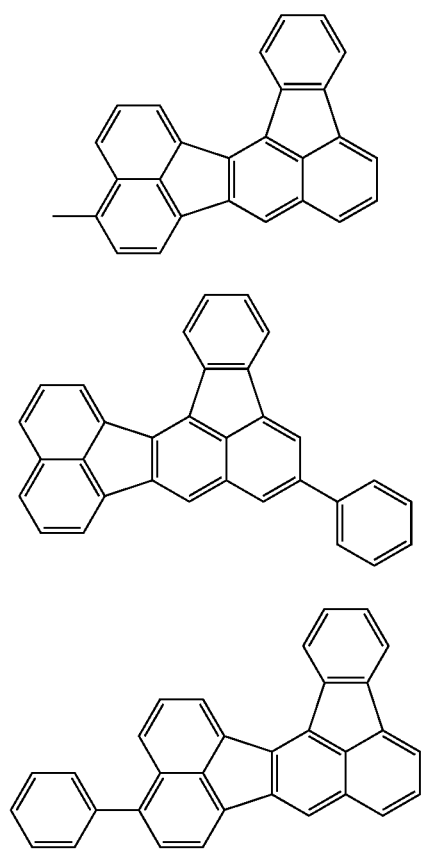
A4
A5
A6
A7
A8
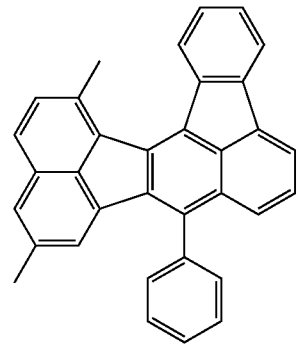
A10
A11
A12
A13
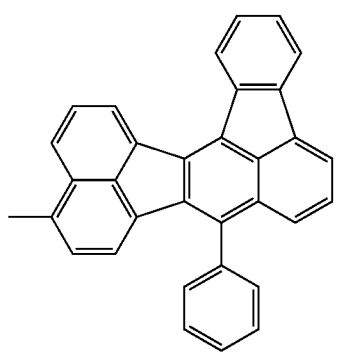

A14 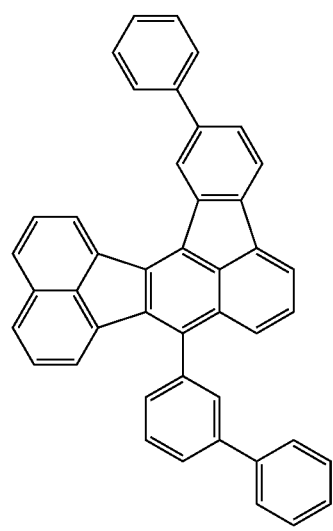
A15 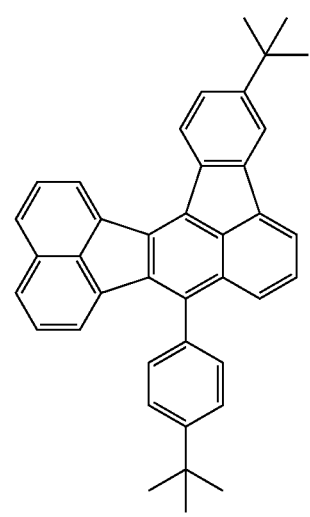
A16 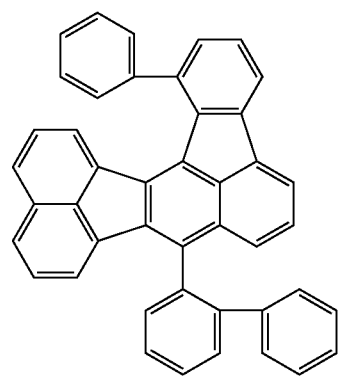
A17 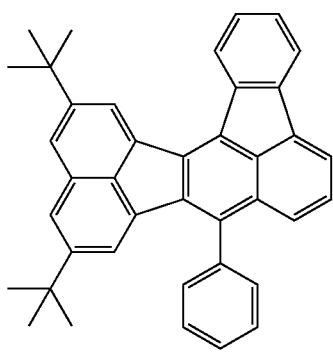
A18 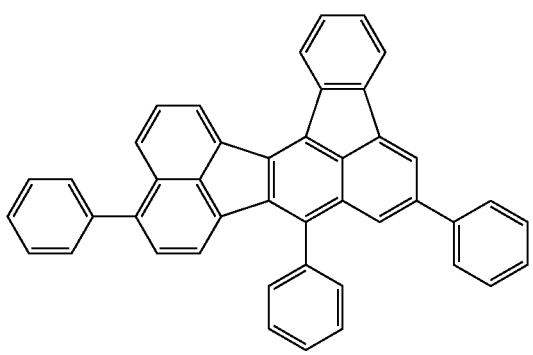
A19 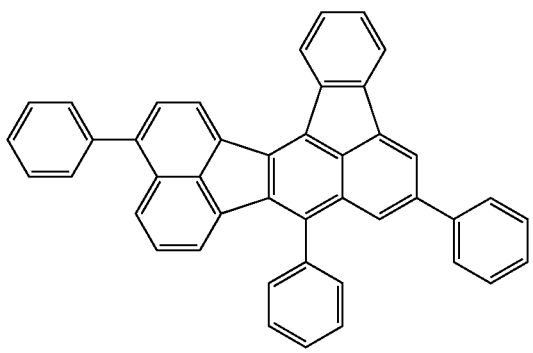
A20 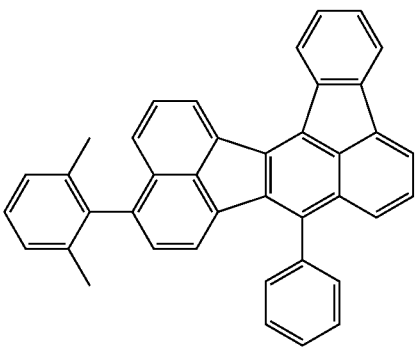

-continued
A21
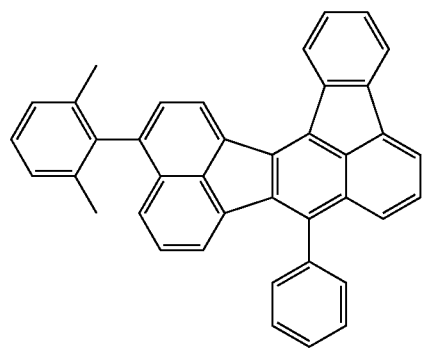
A22
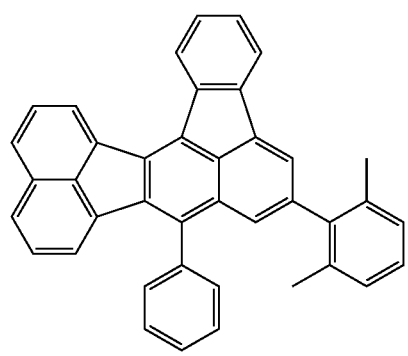
A23
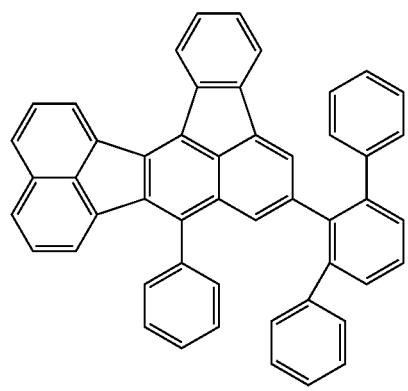
A24
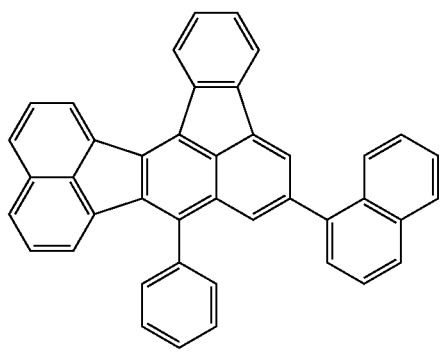
-continued
A25
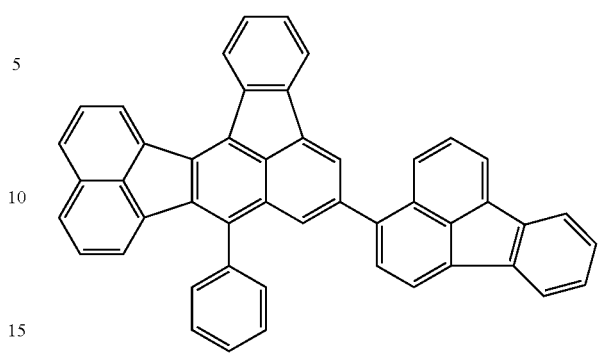
A26
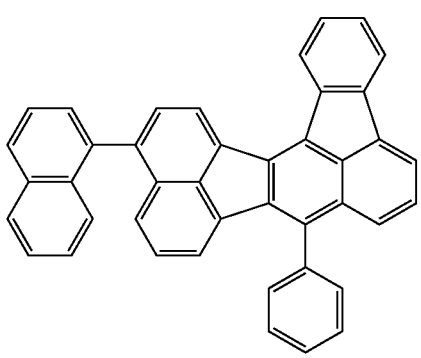
A27
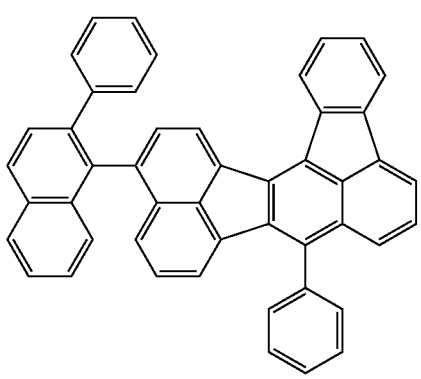
A28
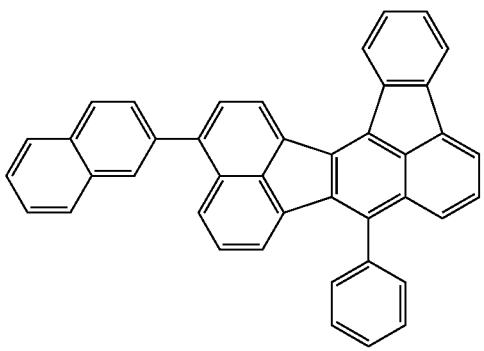

A29
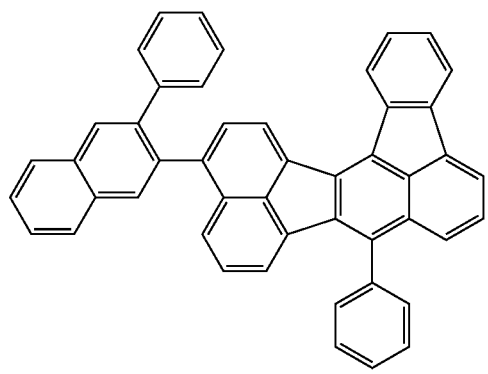
A33
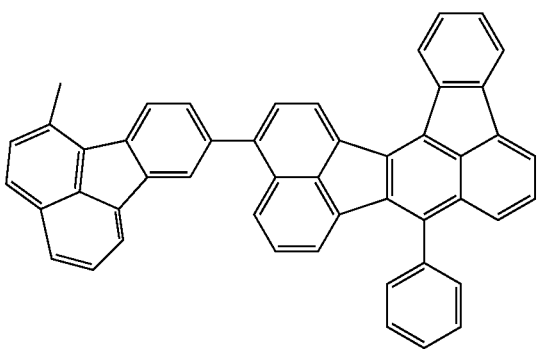
A30
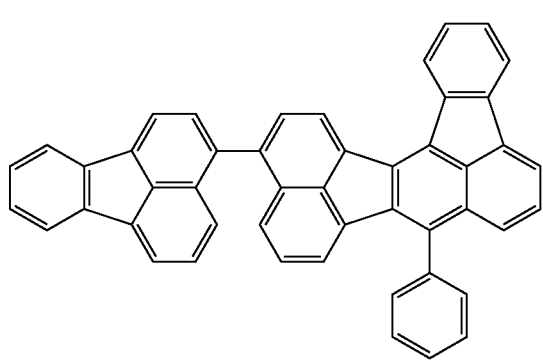
A34
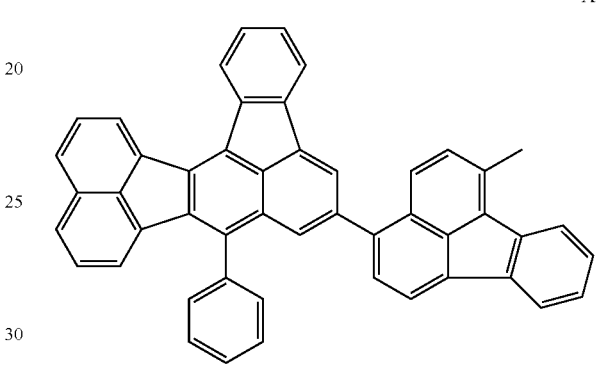
A31
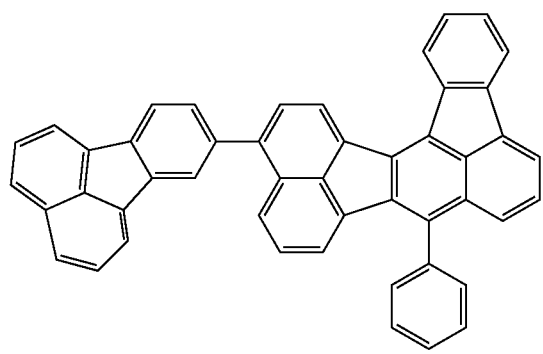
A35
A32
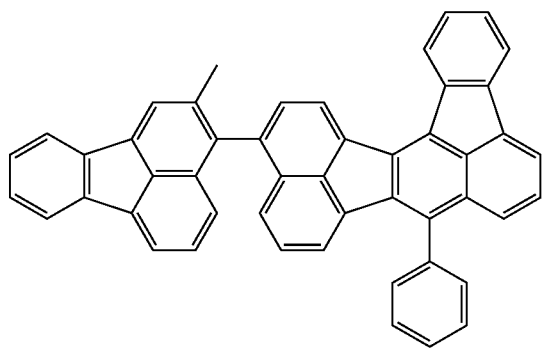
A36
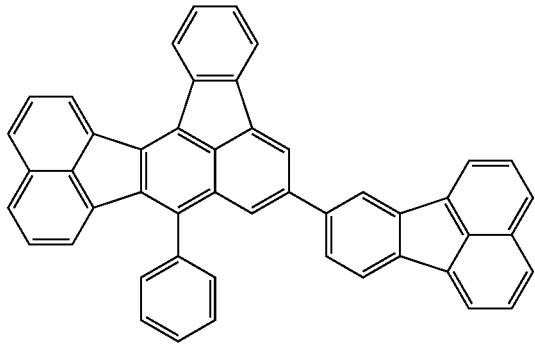

A37
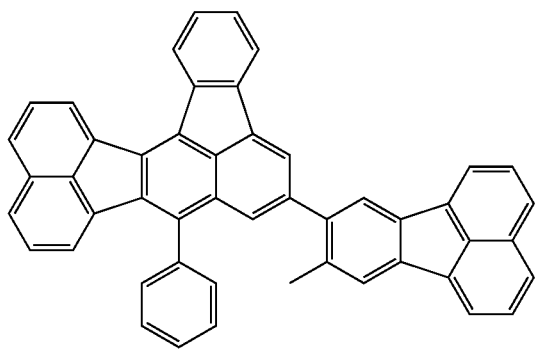
A38
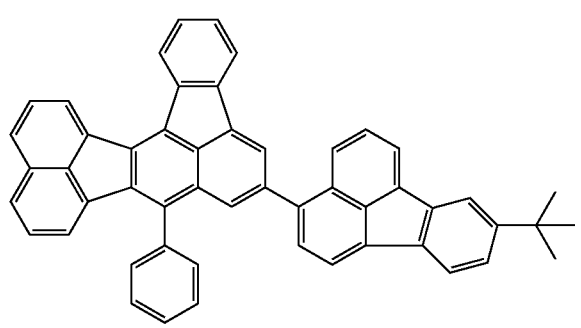
A39
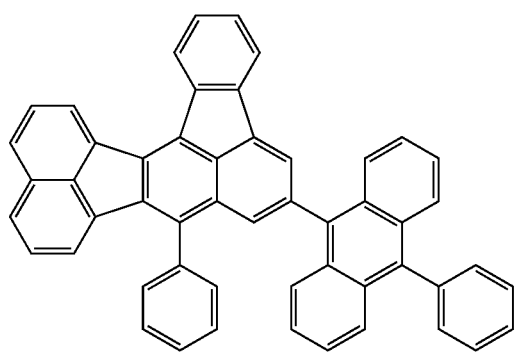
A40
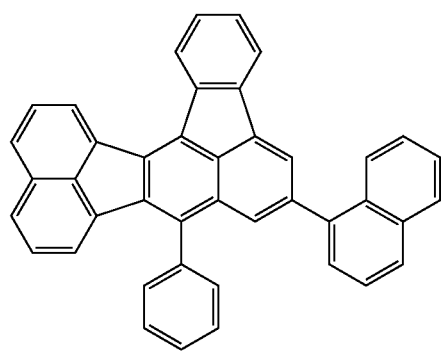
A41
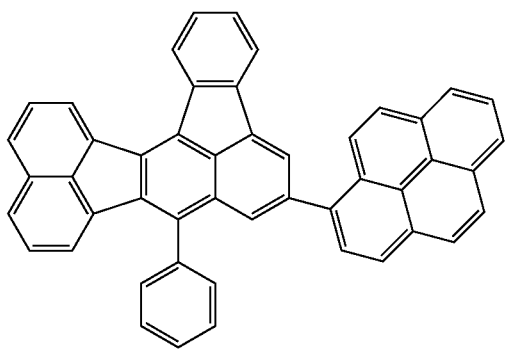
A42
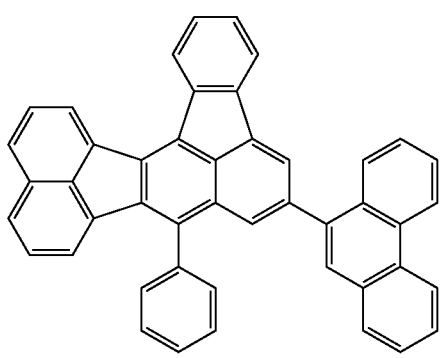
A43
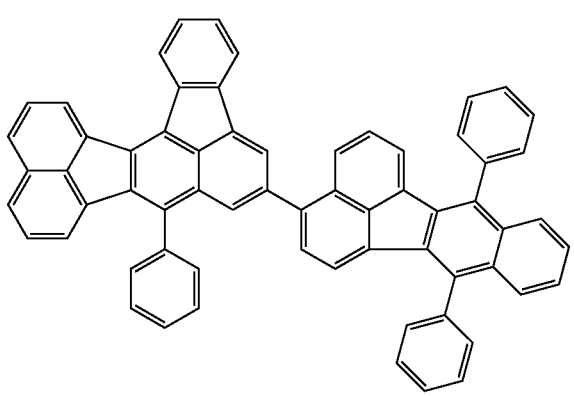
A44
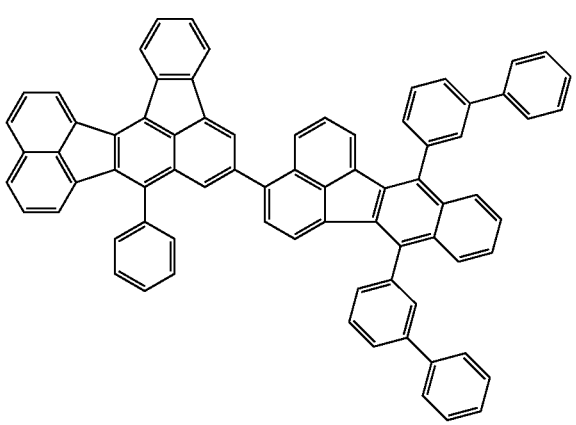

A45
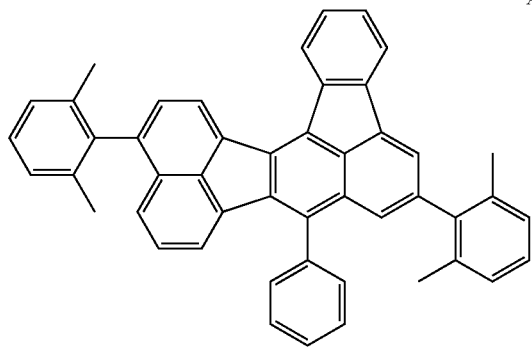
A46
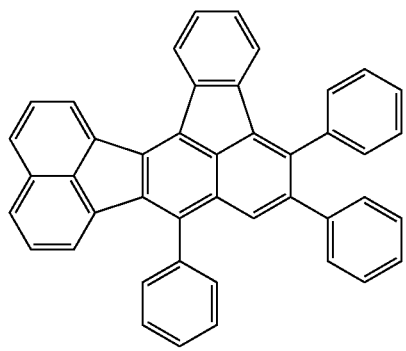
A47
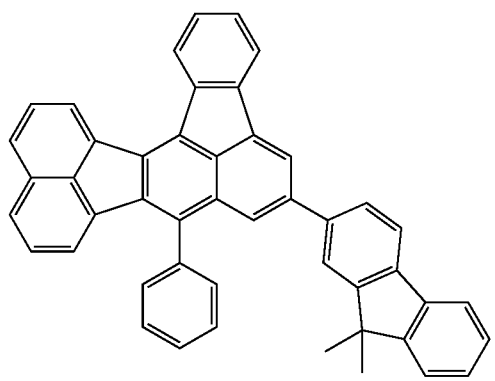
A48
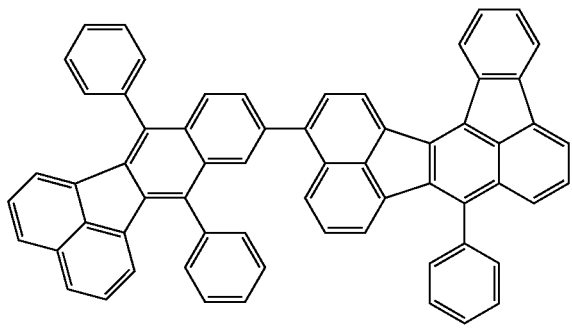
A49
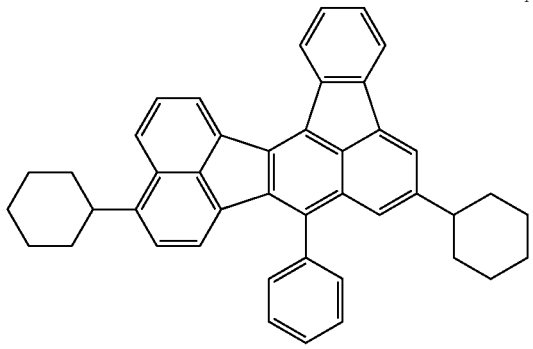
A50
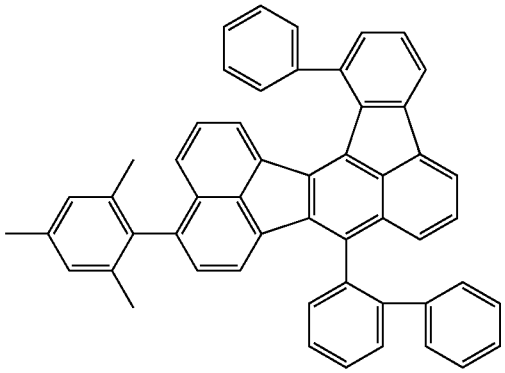
A51
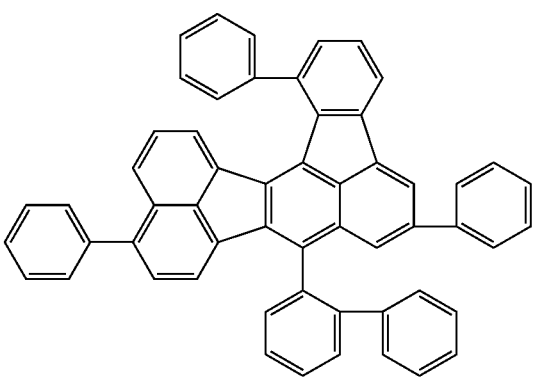
A52
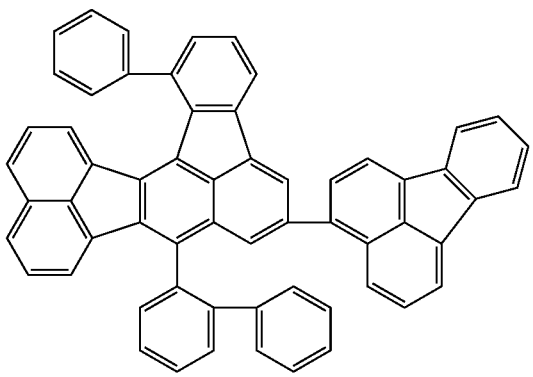

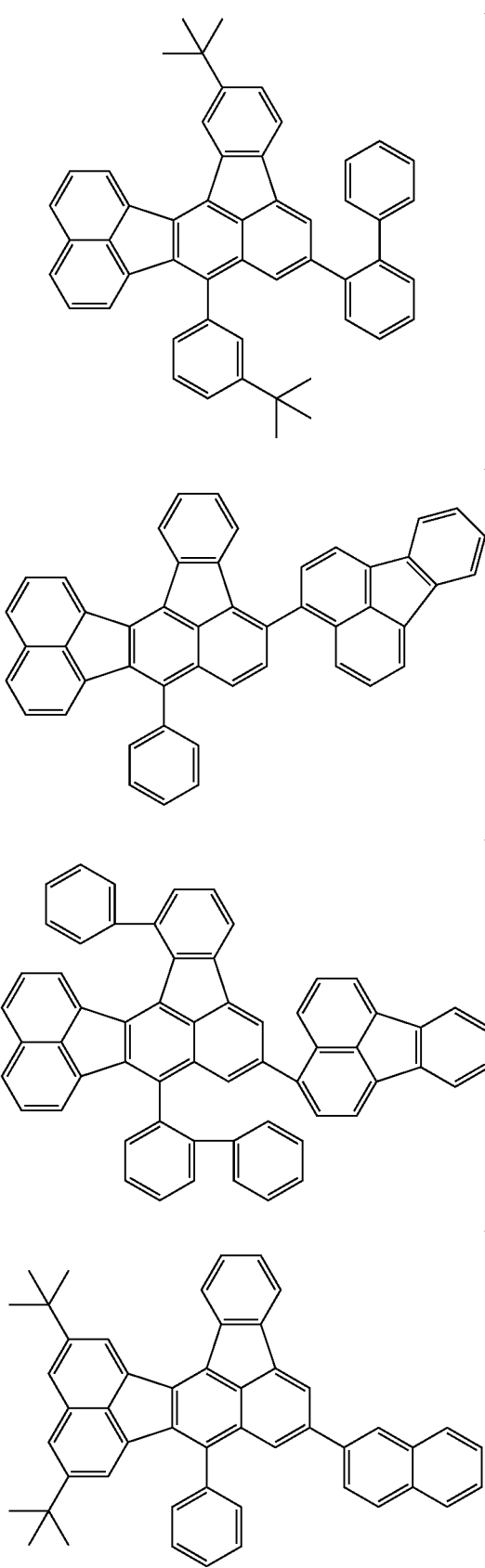
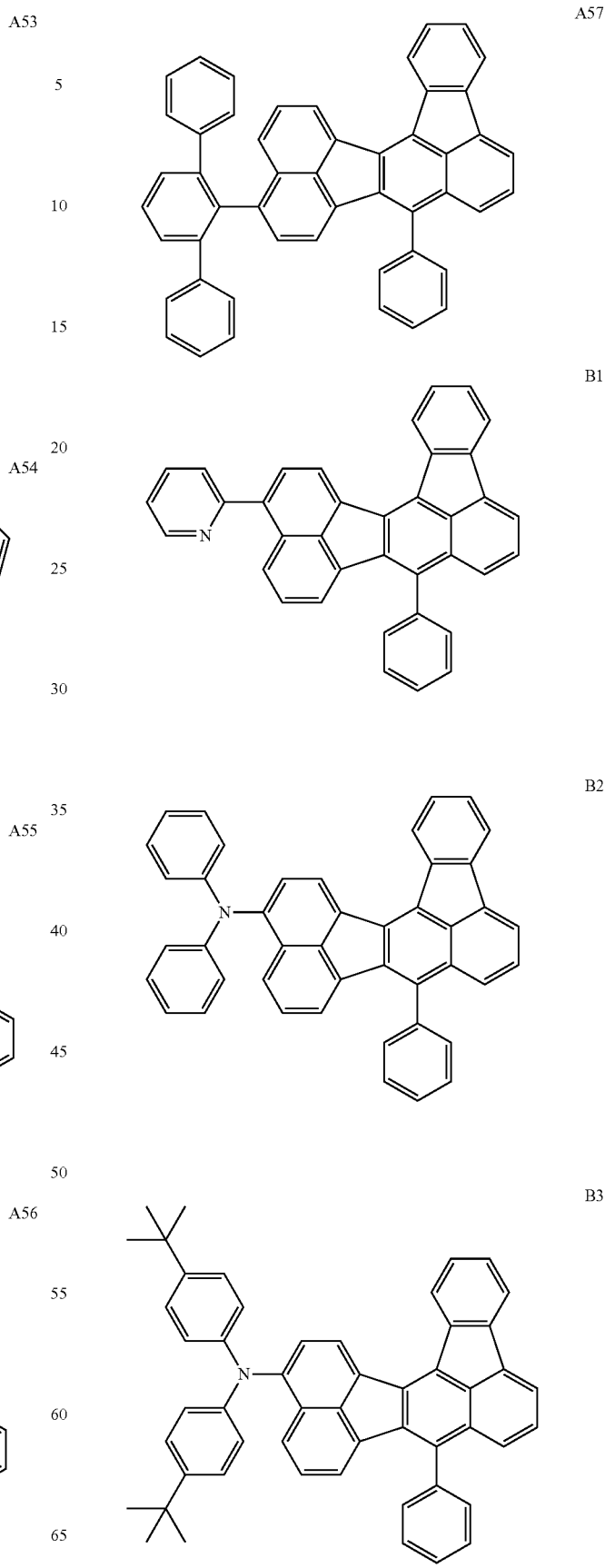

B4
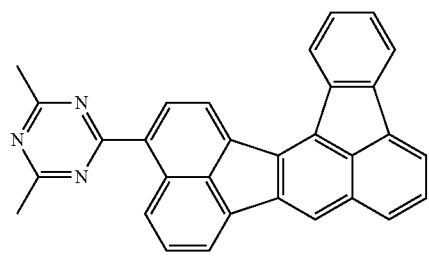
B5
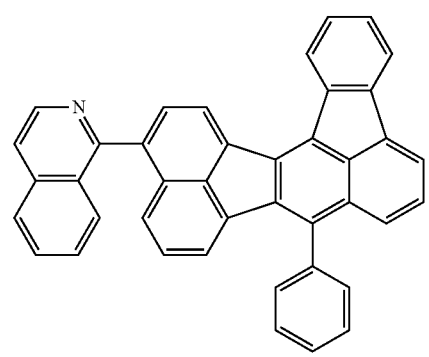
B6
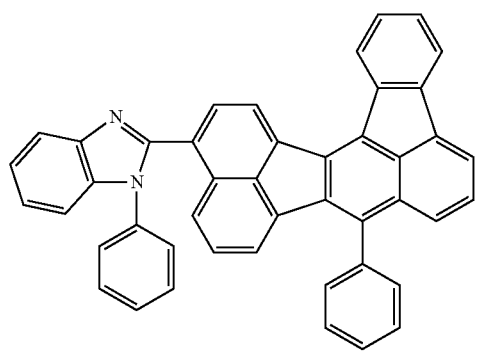
B7
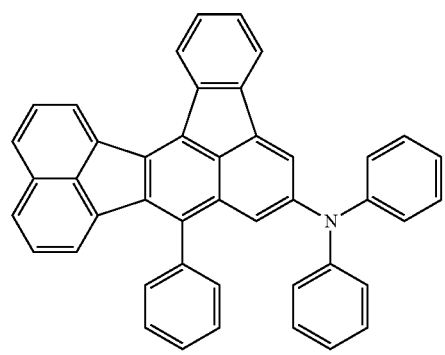
B8
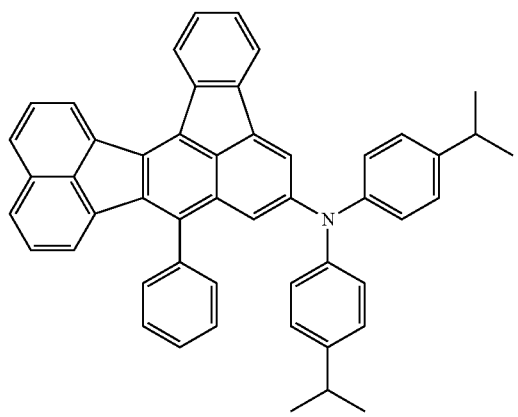
B9
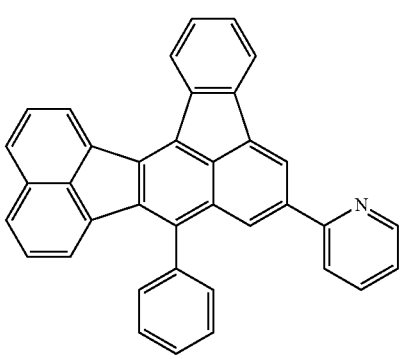
B10
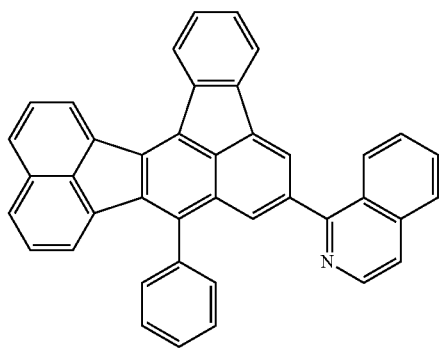
B11
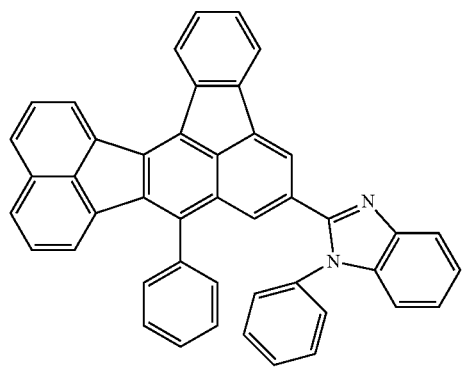

-continued
B12
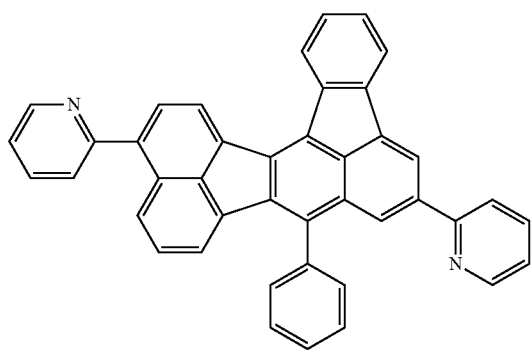
B13
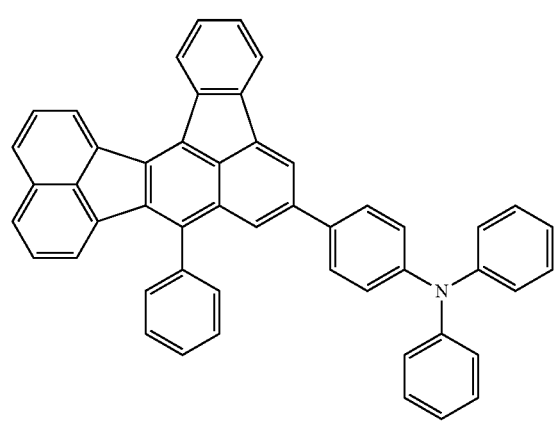
B14
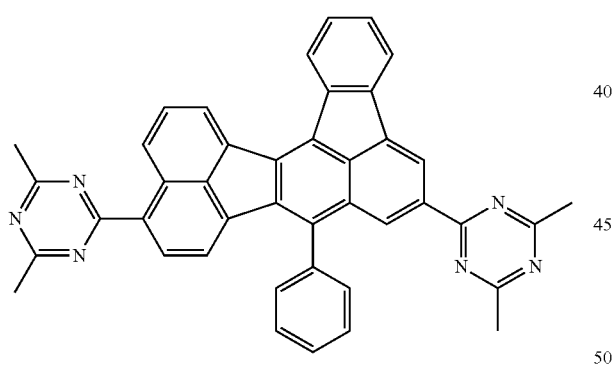
B15
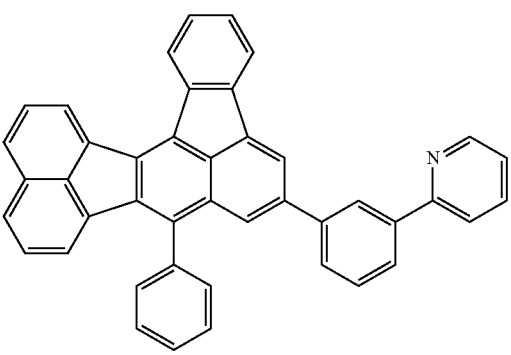
-continued
B16
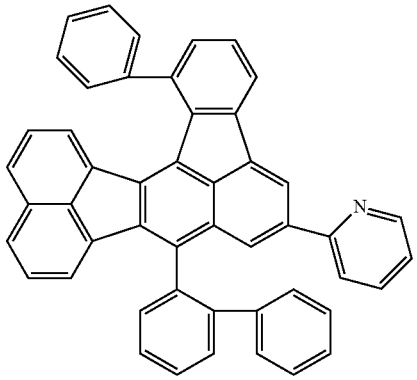
C1
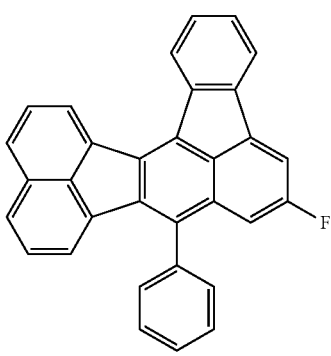
C2
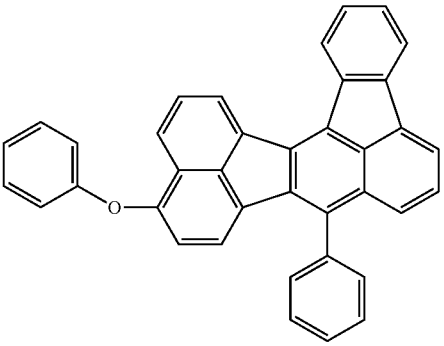
C3
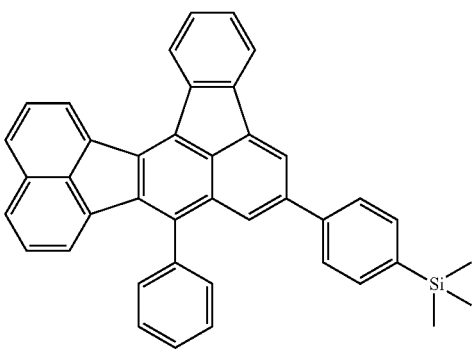

C4

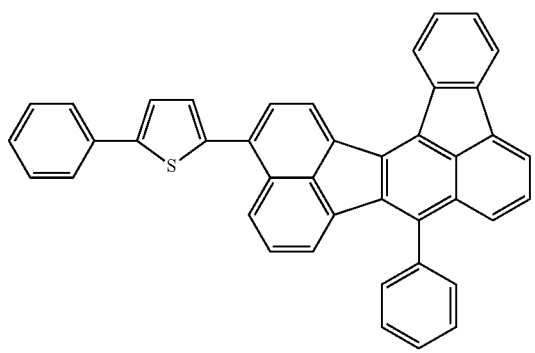

(Properties of Each Exemplified Compound Group)

Among the exemplified compounds, the compounds shown in group A each have a molecule the whole of which is composed of only a hydrocarbon. The compounds composed of only hydrocarbons have low HOMO energy levels. Therefore, the oxidation potential is decreased, and this indicates that the organic compounds are stable to oxidation.

Therefore, among the organic compounds according to the present invention, the compounds shown in group A and composed of only hydrocarbons have high molecular stability.

(Properties of Exemplified Compounds A1 to A57)

Next, more preferred exemplified compounds among the compounds A1 to A57 are described.

When a substituent is introduced into a basic skeleton so as to be perpendicular to the basic skeleton, it has a three-dimensional structure and thus can suppress overlap between molecules, thereby suppressing concentration quenching.

This applies to the compounds shown by A8 to A57 among the exemplified compounds shown by A1 to A57. These compounds can be represented by general formula (2). The compounds represented by general formula (2) are capable of suppressing stacking of molecules by introducing a phenyl group at the $R_4$ position of the general formula (1). Therefore, the compounds have the effect of suppressing quenching due to an increase in concentration.

General Formula (2)

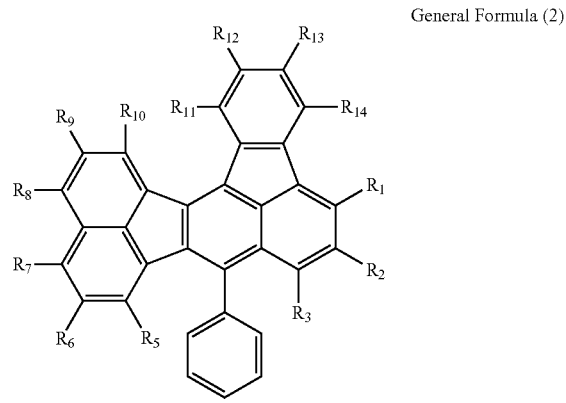

In the general formula (2), $R_1$ to $R_3$ and $R_5$ to $R_{14}$ are each independently selected from a hydrogen atom, an alkyl group, and an aryl group.

(Properties of Exemplified Compounds A8 to A57)

Among the compounds shown by A8 to A57, the compound shown by A18 to A48 and A50 to A57 have an aromatic substituent in a direction in which the conjugation length is long in a conjugation plane of the basic skeleton and thus have high molecular oscillator strength and high quantum yield. These compounds can be represented by general formula (3) below. As shown in the general formula (3), compounds having high quantum yield can be obtained by introducing no substituent other than $R_1$, $R_2$, $R_7$, and $R_8$.

General Formula (3)

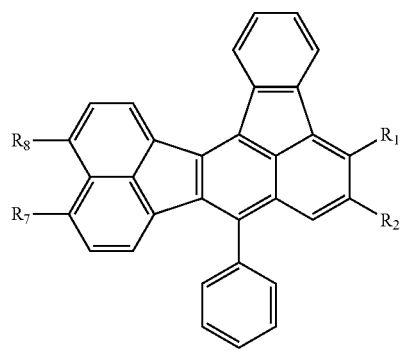

In the general formula (3), $R_1$, $R_2$, $R_7$, and $R_8$ are each independently selected from a hydrogen atom, an alkyl group, and an aryl group. In addition, at least one of these substituents is an aryl group.

(Properties of Exemplified Compounds B1 to B16)

In addition, when a substituent is a nitrogen-containing structure as shown by B1 to B16, the oxidation potential of molecules can be changed due to nitrogen atoms. When a substituent is a nitrogen-containing structure, the maximum light emission wavelength can be shifted to the longer wavelength side. When a substituent is a nitrogen-containing structure, use for applications such as electron-transporting, hole-transporting, and hole-trapping luminescent materials can be realized.

(Properties of Exemplified Compounds C1 to C4)

In addition, when a substituent contains a heteroatom other than nitrogen as shown by C1 to C4, the oxidation potential of molecules is more changed or intermolecular interaction is changed. When a substituent contains a heteroatom other than nitrogen, the maximum light emission wavelength can be shifted to the longer wavelength side. When a substituent contains a heteroatom other than nitrogen, use for applications such as electron-transporting, hole-transporting, and hole-trapping luminescent materials can be realized a high concentration of 100%.

The exemplified compounds are given as groups A to C as described above. These compounds have the basic skeleton which emits blue light. In addition, the basic skeleton of the compounds according to the present invention can emit longer wavelength light than blue light, specifically green light, by providing a substituent. The organic compounds represented by the general formula (1) are not limited to the exemplified compounds and may be used for a host material, an electron transport layer, an electron injection layer, a hole transport layer, a hole injection layer, a hole blocking layer, and the like of an organic light-emitting device. In this case, the emitted light color of the organic light-emitting device is not limited to blue, and more specifically, the color may be green, red, white, or a neutral color. In addition, the compounds can be used as a host material of a light-emitting layer of an organic light-emitting device which emits green light.

(Description of Synthesis Route)

An example of synthesis routes of the organic compounds according to the present invention is described. A reaction formula is described below. An example in which $R_1$, $R_2$, or $R_3$ as a representative substituent is hydrogen or halogen is described. A debromination reaction in the third step in the synthesis route is performed by heating in the presence of a palladium catalyst.

When $R_1$, $R_2$, or $R_3$ is halogen, indenobenzo[k]fluoranthene as the basic skeleton is coupled with arylboronic acid shown by D3 at the halogen position. This permits introduction of various substituents. In this case, $R_4$ represents an aryl group. Although not shown in the formula below, arylamine can be introduced as a substituent by the same method. When a substituent is introduced at a position other than the positions shown by $R_1$ to $R_3$ in the formula below, synthesis can be performed by substituting another substituent for a hydrogen atom at the introduction position. Examples of the substituent include an alkyl group, a halogen atom, a phenyl group, and the like.

Synthesis Route

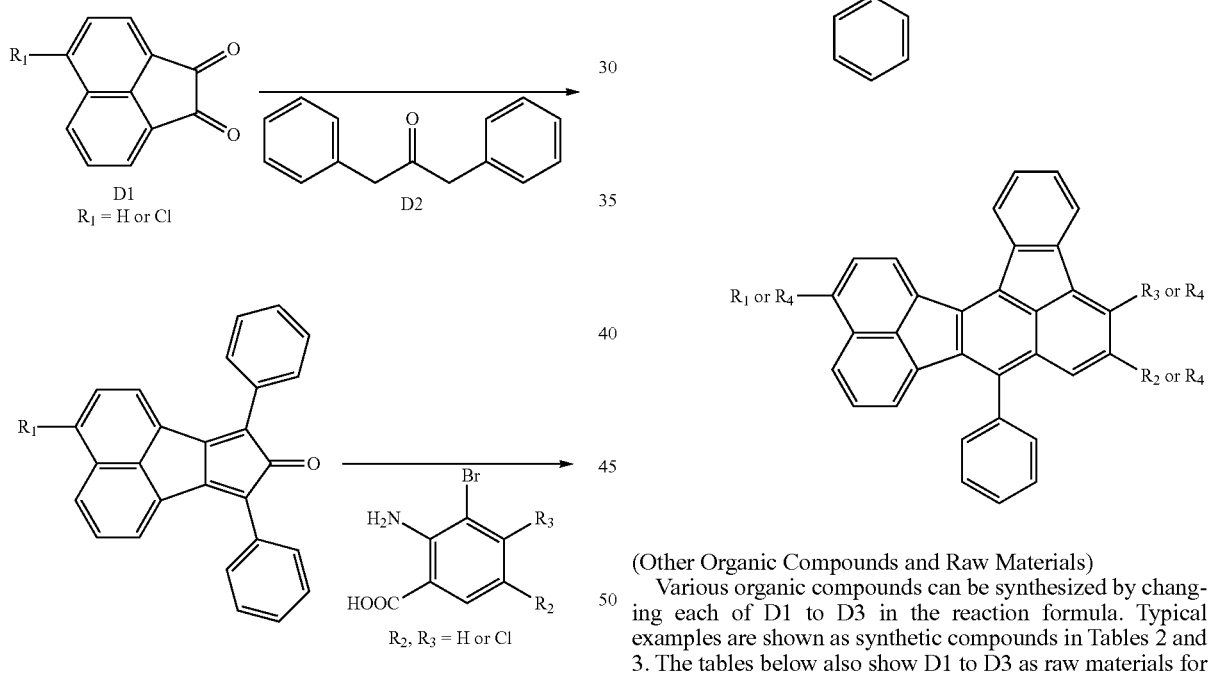

(Other Organic Compounds and Raw Materials)

Various organic compounds can be synthesized by changing each of D1 to D3 in the reaction formula. Typical examples are shown as synthetic compounds in Tables 2 and 3. The tables below also show D1 to D3 as raw materials for producing the synthetic compounds.

TABLE 2

| Synthesis example | D1 | D2 | D3 |
|---|---|---|---|
| 1 | (structure) | (structure) | — |

TABLE 2-continued
| | | | |
|---|---|---|---|
| 2 | 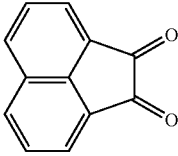 | 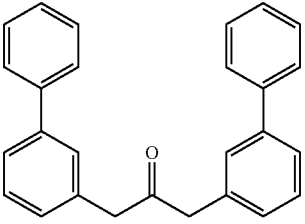 | — |
| 3 | 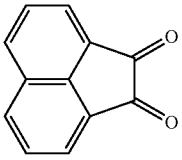 | 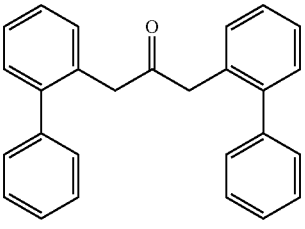 | — |
| 4 | 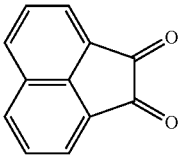 | 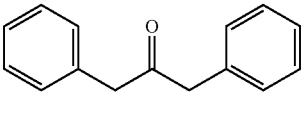 | 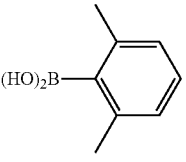 |
| 5 | 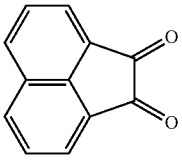 | 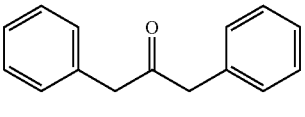 | 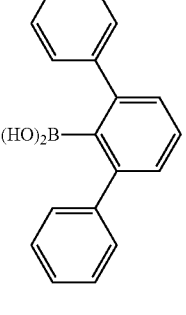 |
| 6 | 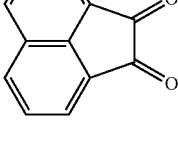 | 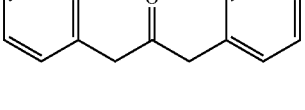 | 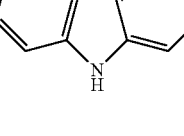 |
| 7 | 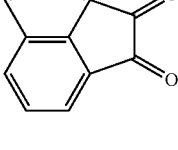 | 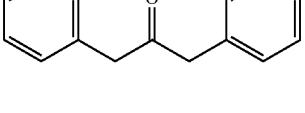 | 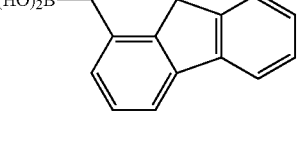 |
| 8 | 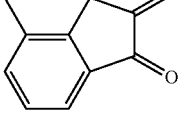 | 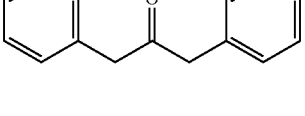 | 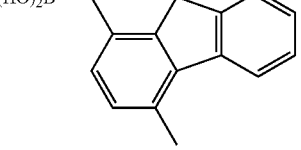 |

TABLE 2-continued
| | | | |
|---|---|---|---|
| 9 | 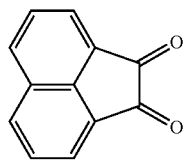 | 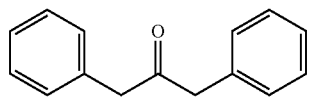 | 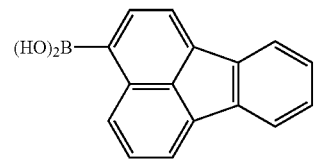 |
| 10 | 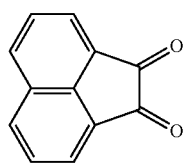 | 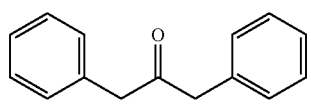 | 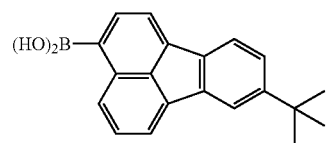 |
| 11 | 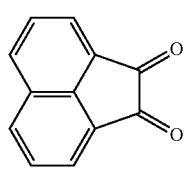 | 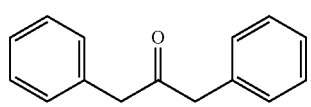 | 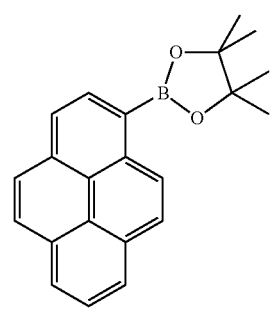 |
| 12 | 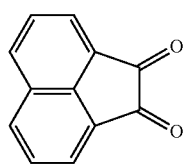 | 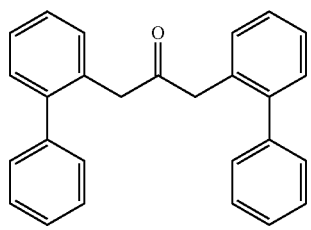 | 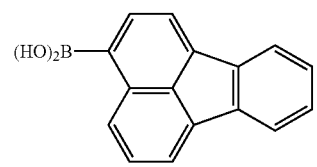 |
| 13 | 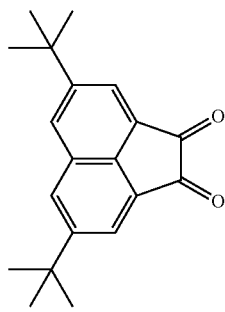 | 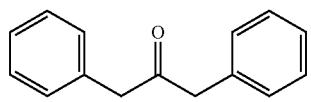 | 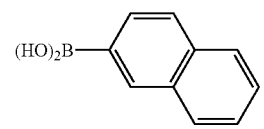 |
| 14 | 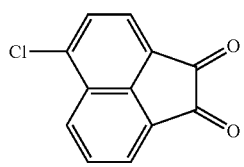 | 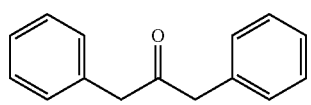 | 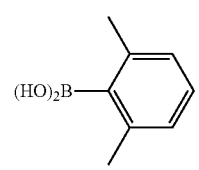 |

TABLE 2-continued
| Synthesis example | Synthetic compound | Exemplified compound No. |
|---|---|---|
| 1 | 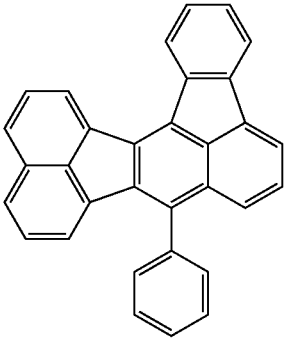 [SMILES: c1ccc(-c2c3cccc4c5ccccc5c(c34)c3c4cccc5cccc(c23)c54)cc1] | A8 |
| 2 | 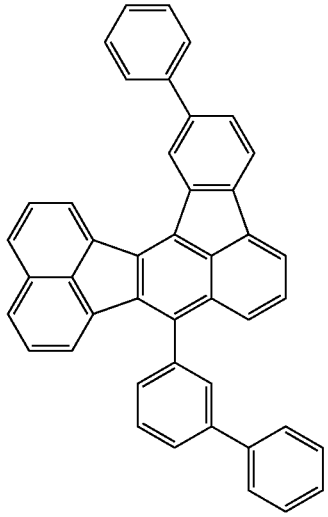 [SMILES: c1ccc(-c2cccc(-c3c4cccc5c6ccc(-c7ccccc7)cc6c(c45)c4c5cccc6cccc(c34)c65)c2)cc1] | A16 |
| 3 | 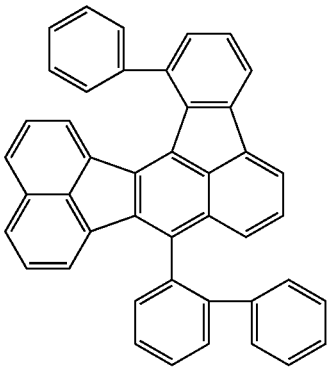 [SMILES: c1ccc(-c2ccccc2-c2c3cccc4c5cccc(-c6ccccc6)c5c(c34)c3c4cccc5cccc(c23)c54)cc1] | A16 |

TABLE 2-continued
| | | |
|---|---|---|
| 4 | 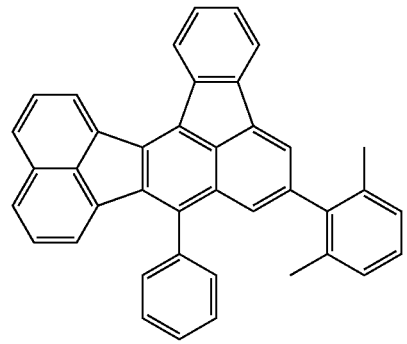 [SMILES: Cc1cccc(C)c1-c1cc2c(-c3ccccc3)c3c4cccc5cccc(c54)c3c3c4ccccc4c(c1)c23] | A22 |
| 5 | 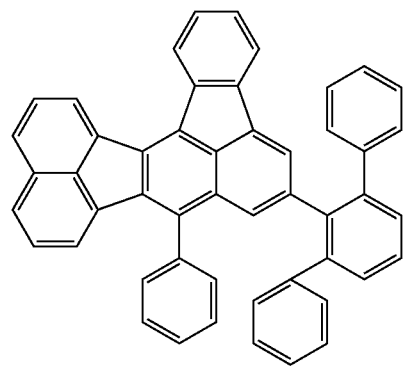 [SMILES: c1ccc(-c2cccc(-c3ccccc3)c2-c2cc3c(-c4ccccc4)c4c5cccc6cccc(c65)c4c4c5ccccc5c(c2)c34)cc1] | A23 |
| 6 | 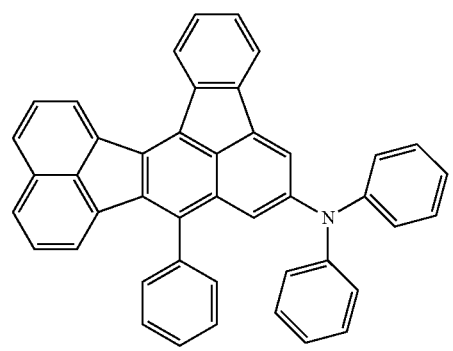 [SMILES: c1ccc(-c2c3cc(N(c4ccccc4)c4ccccc4)cc4c5ccccc5c(c34)c3c4cccc5cccc(c23)c54)cc1] | D7 |
| 7 | 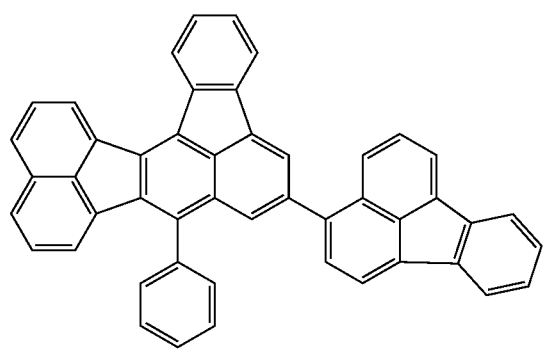 [SMILES: c1ccc(-c2c3cc(-c4ccc5c6c(cccc46)-c4ccccc4-5)cc4c5ccccc5c(c34)c3c4cccc5cccc(c23)c54)cc1] | A25 |

TABLE 2-continued
| | | |
|---|---|---|
| 8 | 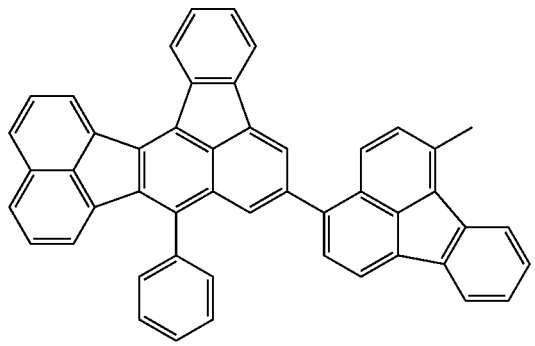 [SMILES: Cc1ccc2c(-c3cc4c(-c5ccccc5)c5c6cccc7cccc(c76)c5c5c6ccccc6c(c3)c45)ccc3c2c1-c1ccccc1-3] | A34 |
| 9 | 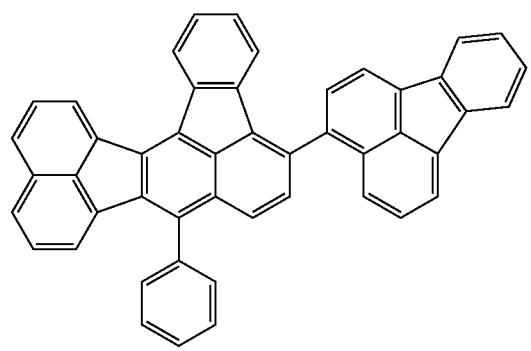 [SMILES: c1ccc(-c2c3ccc(-c4ccc5c6c(cccc46)-c4ccccc4-5)c4c5ccccc5c(c34)c3c4cccc5cccc(c23)c54)cc1] | A54 |
| 10 | 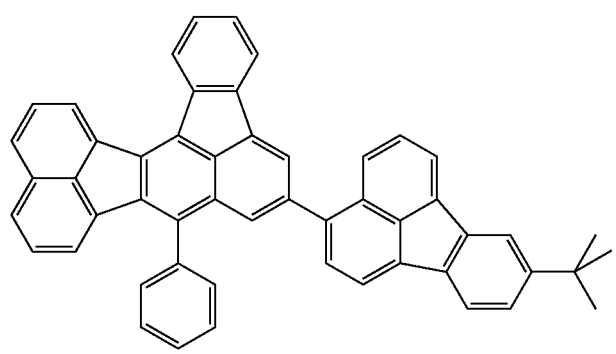 [SMILES: CC(C)(C)c1ccc2c(c1)-c1cccc3c(-c4cc5c(-c6ccccc6)c6c7cccc8cccc(c87)c6c6c7ccccc7c(c4)c56)ccc-2c13] | A38 |
| 11 | 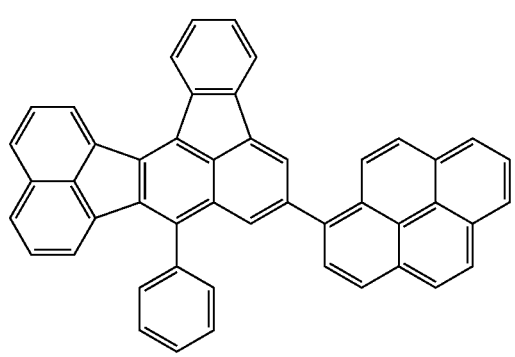 [SMILES: c1ccc(-c2c3cc(-c4ccc5ccc6cccc7ccc4c5c67)cc4c5ccccc5c(c34)c3c4cccc5cccc(c23)c54)cc1] | A41 |

TABLE 2-continued
| 12 | 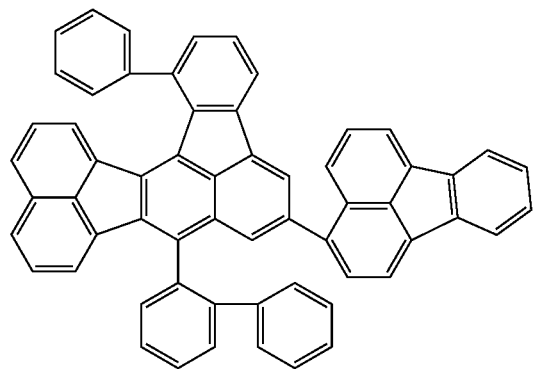 [SMILES: c1ccc(-c2ccccc2-c2c3cc(-c4ccc5c6c(cccc46)-c4ccccc4-5)cc4c5cccc(-c6ccccc6)c5c(c34)c3c4cccc5cccc(c23)c54)cc1] | A55 |
| 13 | 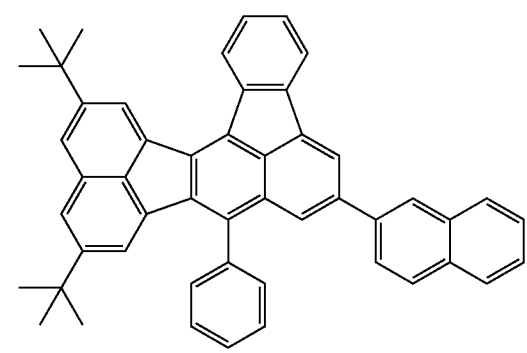 [SMILES: CC(C)(C)c1cc2cc(C(C)(C)C)cc3c2c(c1)c1c(-c2ccccc2)c2cc(-c4ccc5ccccc5c4)cc4c5ccccc5c(c24)c31] | A56 |
| 14 | 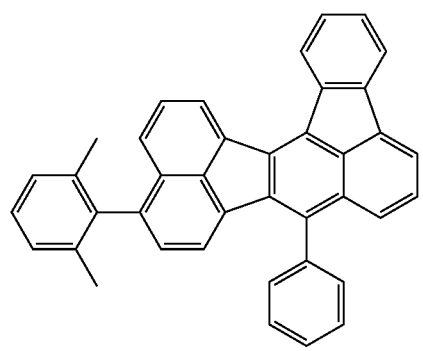 [SMILES: Cc1cccc(C)c1-c1ccc2c3c(-c4ccccc4)c4cccc5c6ccccc6c(c45)c3c3cccc1c23] | A20 |
TABLE 3
| Synthesis example | D1 | D2 | D3 |
|---|---|---|---|
| 15 | 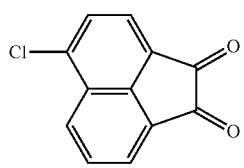 | 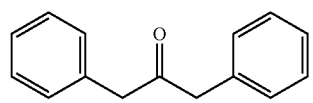 | 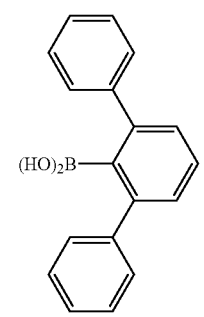 |

TABLE 3-continued

| Synthesis example | D1 | D2 | D3 |
|---|---|---|---|
| 16 | 5-chloroacenaphthylene-1,2-dione | 1,3-diphenylpropan-2-one | fluoranthen-3-ylboronic acid |
| 17 | 5-chloroacenaphthylene-1,2-dione | 1,3-diphenylpropan-2-one | (1-methylfluoranthen-8-yl)boronic acid |
| 18 | 5-chloroacenaphthylene-1,2-dione | 1,3-diphenylpropan-2-one | bis(4-tert-butylphenyl)amine |
| 19 | 5-chloroacenaphthylene-1,2-dione | 1,3-diphenylpropan-2-one | pyridin-2-ylzinc bromide |
| 20 | 5-chloroacenaphthylene-1,2-dione | 1,3-bis(biphenyl-2-yl)propan-2-one | (2,4,6-trimethylphenyl)boronic acid |
| 21 | 5-chloroacenaphthylene-1,2-dione | 1,3-diphenylpropan-2-one | phenylboronic acid |
| 22 | 5-chloroacenaphthylene-1,2-dione | 1,3-diphenylpropan-2-one | (2,6-dimethylphenyl)boronic acid |

TABLE 3-continued

| Synthesis example | D1 | D2 | D3 |
|---|---|---|---|
| | Synthesis example | Synthetic compound | Exemplified compound No. |
| | 15 | | A57 |
| | 16 | | A30 |
| | 17 | | A33 |
| | 18 | | B3 |

TABLE 3-continued
| Synthesis example | D1 | D2 | D3 |
|---|---|---|---|
| 19 | | 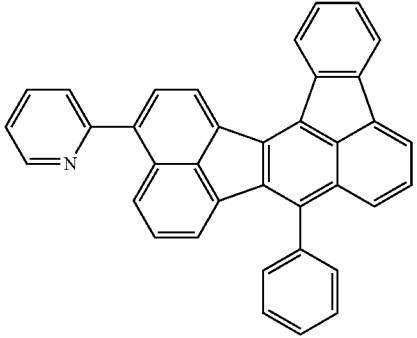 | B1 |
| 20 | | 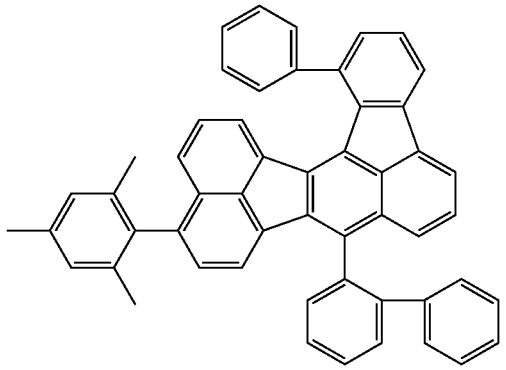 | A50 |
| 21 | | 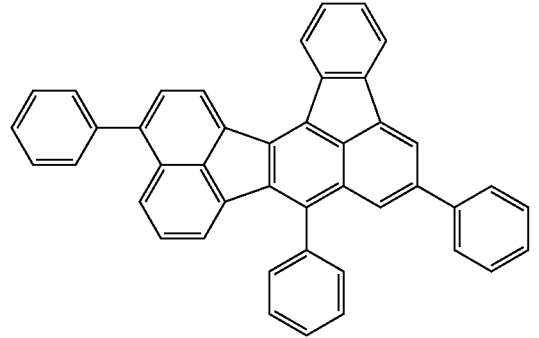 | A18 |
| 22 | | 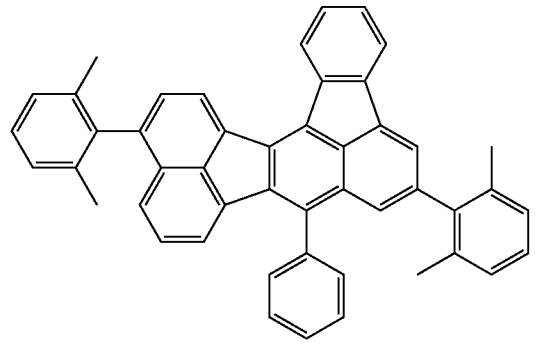 | A45 |

(Description of Organic Light-Emitting Device)

Next, an organic light-emitting device according to the present invention is described.

The organic light-emitting device according to the present invention includes at least a pair of electrodes, i.e., an anode and a cathode, and an organic compound layer disposed between the electrodes. The organic compound layer contains an organic compound represented by the general formula (1). The organic light-emitting device is a device in which carriers are injected from the anode and the cathode to generate excitons of a luminescent organic compound in the organic compound layer so that light is emitted when the excitons return to the ground state.

When the organic compound layer serves as a light-emitting layer, the light-emitting layer may include only an organic compound according to the present invention or another component may be present in the light-emitting layer.

When the light-emitting layer may partially contain an organic compound according to the present invention, the organic compound according to the present invention may be either a main component or a sub-component in the light-emitting layer.

With respect to the main component and the sub-component, a component at the highest weight ratio among the compounds constituting the light-emitting layer is referred to as the "main component", and a component at a lower weight ratio than the main component is referred to as the "sub-component".

A material for the main component can be referred to as a "host material".

A material for the sub-component is a dopant (guest) material. Other materials which can be used as the sub-component include a luminescent assist material and a charge-injecting material.

When the compound according to the present invention is used as the guest material, the concentration of the guest material is preferably 0.01 wt % or more and 20 wt % or less, more preferably 0.5 wt % or more and 10 wt % or less, relative to the host material.

As a result of various investigations, the inventors have found that a device using an organic compound represented by the general formula (1) of the present invention as a host material or guest material, particularly a guest material, of a light-emitting layer has optical output with high efficiency and high luminance and very high durability.

An example of organic light-emitting devices using the organic compounds according to the present invention is described below.

The organic light-emitting devices manufactured using the organic compounds according to the present invention include a device configured by providing in turn an anode, a light-emitting layer, and a cathode on a substrate. Also, the organic light-emitting devices include a device configured by providing in turn an anode, a hole transport layer, an electron transport layer, and a cathode. Further, the organic light-emitting devices include a device configured by providing in turn an anode, a hole transport layer, a light-emitting layer, an electron transport layer, and a cathode, a device configured by providing in turn an anode, a hole injection layer, a hole transport layer, a light-emitting layer, an electron transport layer, and a cathode, and a device configured by providing in turn an anode, a hole transport layer, a light-emitting layer, a hole/exciton blocking layer, an electron transport layer, and a cathode. However, these five examples of multilayer type are only basic device configurations, and the configurations of the organic light-emitting devices using the organic compounds according to the present invention are not limited to these. Various layer configurations can be made by, for example, providing an insulating layer at an interface between an electrode and an organic compound layer, providing an adhesive layer or interference layer, providing an electron transport layer or a hole transport layer including two layers having different ionization potentials, etc.

The organic compounds represented by the general formula (1) according to the present invention can be used in the organic compound layer of the light-emitting device with any one of the layer configurations.

The organic compounds of the present invention can be used together with a known low molecular or high molecular hole-injecting compound or transporting compound, a host compound as a host material, a luminescent compound, an electron-injecting compound or electron-transporting compound, or the like according to demand.

Examples of these compounds are given below.

As the hole-injecting compound or hole-transporting compound, a material with high hole mobility can be used. Low molecular or high molecular materials having the hole-injecting ability or hole-transporting ability include triarylamine derivatives, phenylenediamine derivatives, stilbene derivatives, phthalocyanine derivatives, porphyrin derivatives, poly (vinylcarbazole), poly(thiophene), and other conductive polymers. Of course, such materials are not limited to these.

Specific structural formulae of the host compound are shown in Table 4. The host compound may be a derivative having any of the structural formulae shown in Table 4. Other host compounds include condensed ring compounds (e.g., fluorene derivatives, naphthalene derivatives, anthracene derivative, pyrene derivatives, carbazole derivatives, quinoxaline derivatives, quinoline derivatives, and the like), organic aluminum complexes such as tris(8-quinolinolate) aluminum and the like, organic zinc complexes, triphenylamine derivatives, and polymer derivatives such as poly (fluorene) derivatives, poly(phenylene) derivatives, and the like. Of course, the host compound is not limited to these compounds.

TABLE 4

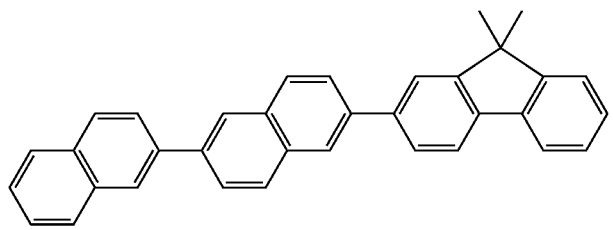 [SMILES: CC1(C)c2ccccc2-c2ccc(-c3ccc4cc(-c5ccc6ccccc6c5)ccc4c3)cc21]

H1

TABLE 4-continued
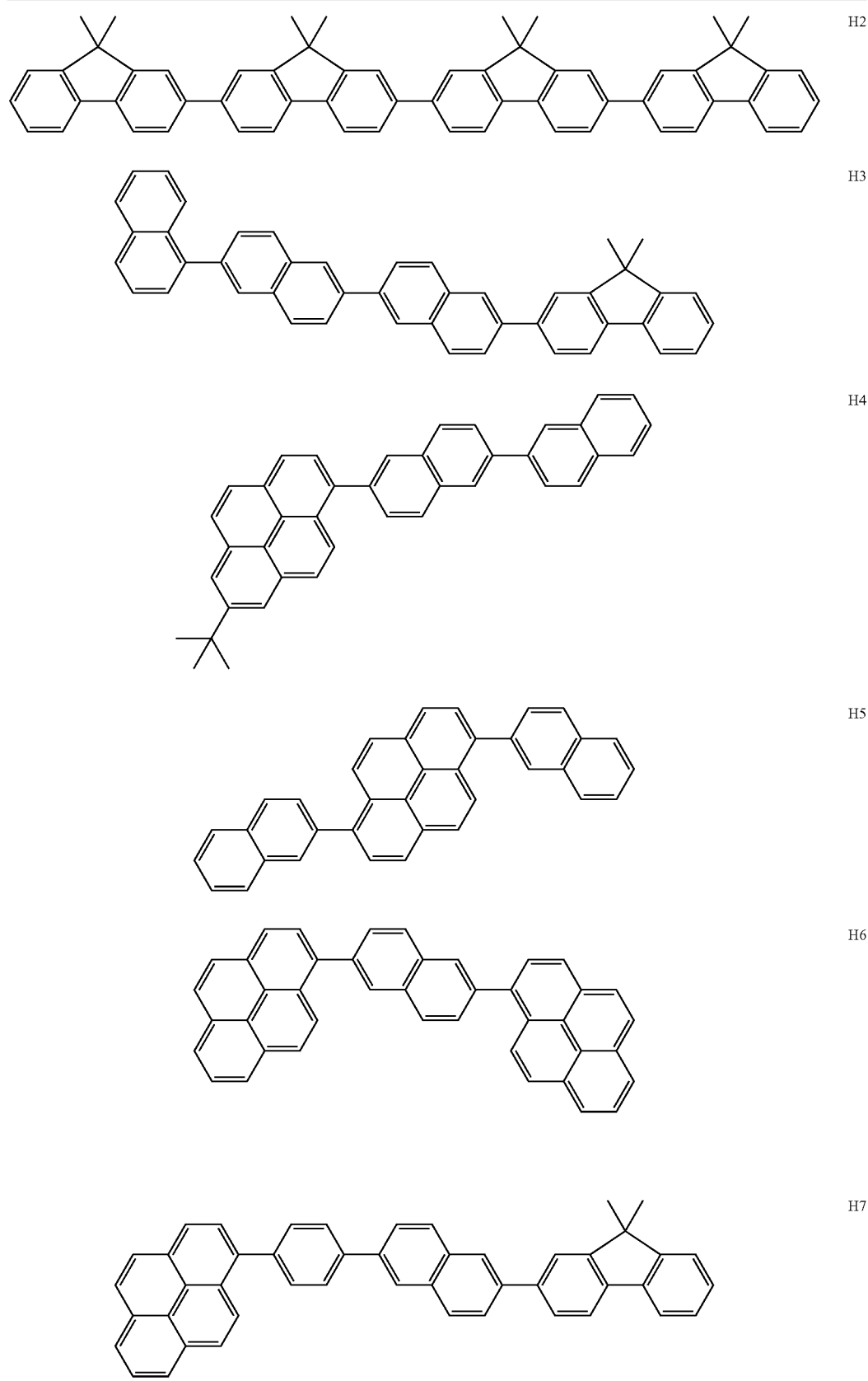

TABLE 4-continued
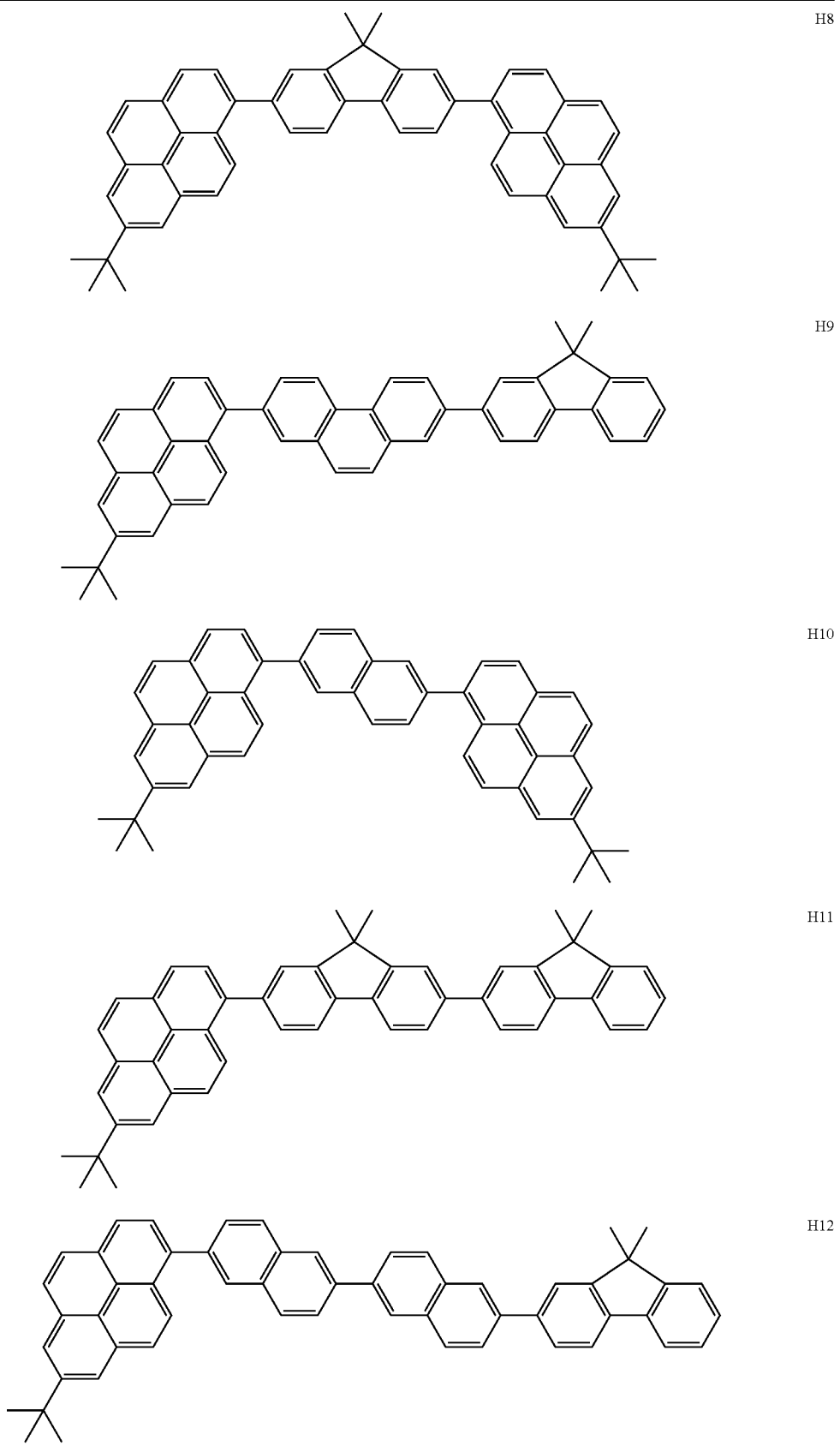

TABLE 4-continued
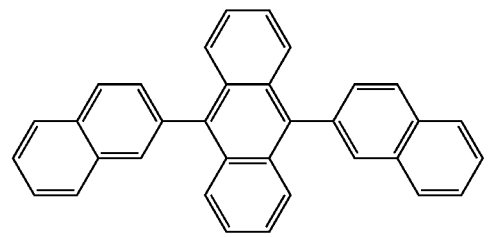 [SMILES: c1ccc2cc(-c3c4ccccc4c(-c4ccc5ccccc5c4)c4ccccc34)ccc2c1] H13
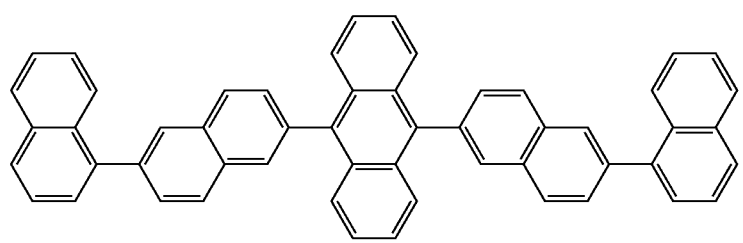 [SMILES: c1ccc2c(-c3ccc4cc(-c5c6ccccc6c(-c6ccc7cc(-c8cccc9ccccc89)ccc7c6)c6ccccc56)ccc4c3)cccc2c1] H14
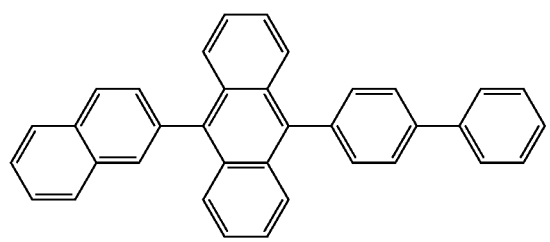 [SMILES: c1ccc(-c2ccc(-c3c4ccccc4c(-c4ccc5ccccc5c4)c4ccccc34)cc2)cc1] H15
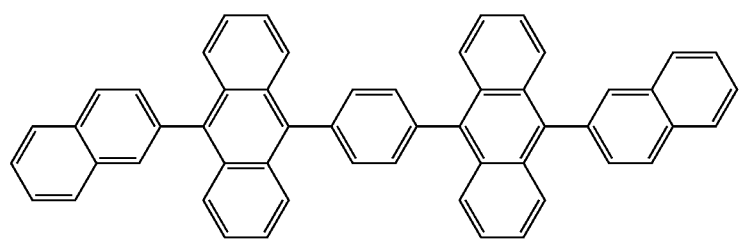 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H16
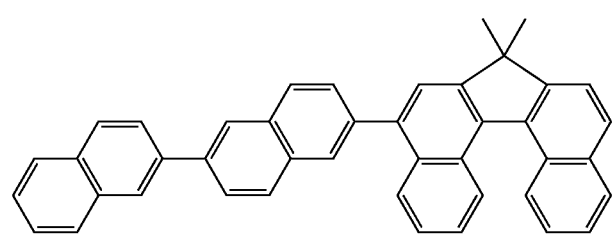 [SMILES: CC1(C)c2ccc3ccccc3c2-c2c1cc(-c1ccc3cc(-c4ccc5ccccc5c4)ccc3c1)c1ccccc21] H17

TABLE 4-continued
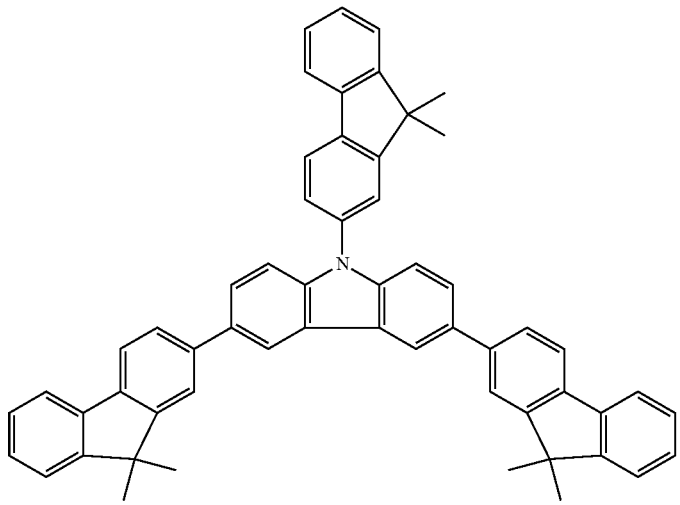 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18
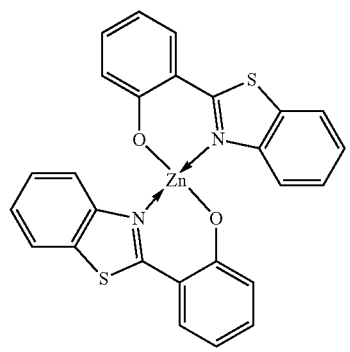
H19
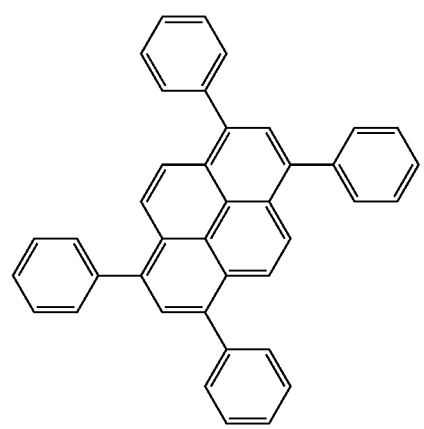 [SMILES: c1ccc(-c2cc(-c3ccccc3)c3ccc4c(-c5ccccc5)cc(-c5ccccc5)c5ccc2c3c54)cc1]
H20
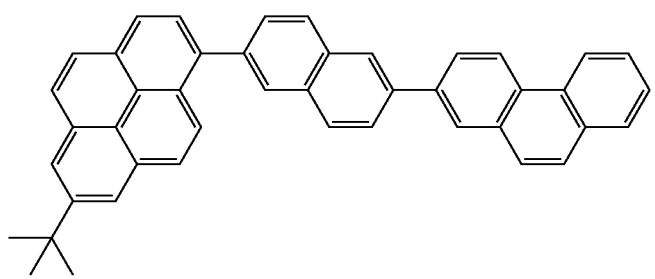 [SMILES: CC(C)(C)c1cc2ccc3ccc(-c4ccc5cc(-c6ccc7c(ccc8ccccc87)c6)ccc5c4)c4ccc(c1)c2c34]
H21

TABLE 4-continued
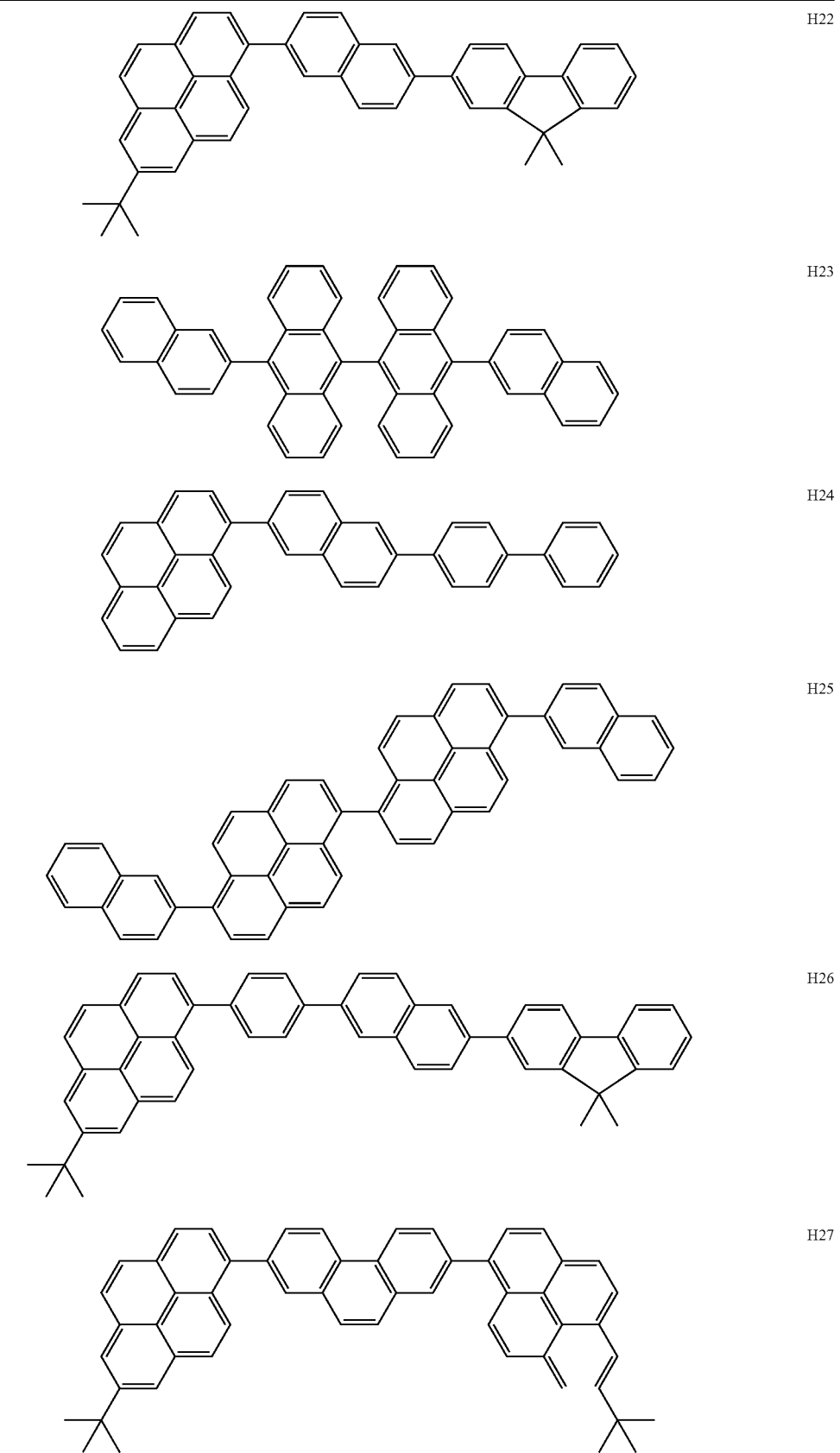

TABLE 4-continued

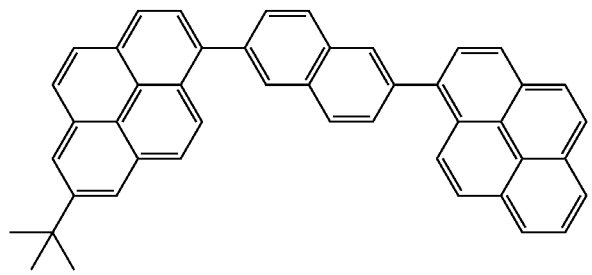 [SMILES: CC(C)(C)c1cc2ccc3ccc(-c4ccc5cc(-c6ccc7ccc8cccc9ccc6c7c89)ccc5c4)c4ccc(c1)c2c34]

H28

The electron-injecting compound or electron-transporting compound is selected in consideration of balance with the hole mobility of the hole-injecting compound or hole-transporting compound, and the like. Compounds having the electron-injecting ability or electron-transporting ability include oxadiazole derivatives, oxazole derivatives, pyrazine derivatives, triazole derivatives, triazine derivatives, quinoline derivatives, quinoxaline derivatives, phenanthroline derivatives, organic aluminum complexes, and the like. Of course, such compounds are not limited to these.

As an anode material, a material having as high a work function as possible can be used. Examples of such a material include elemental metals such as gold, platinum, silver, copper, nickel, palladium, cobalt, selenium, vanadium, tungsten, and the like; alloys of these metals; and metal oxides such as tin oxide, zinc oxide, indium oxide, indium tin oxide (ITO), indium zinc oxide, and the like. In addition, conductive polymers such as polyaniline, polypyrrole, polythiophene, and the like may be used. These electrode materials may be used alone or in combination of two or more. The anode may include a single layer or multiple layers.

On the other hand, as a cathode material, a material having a low work function can be used. Examples of such a material include alkali metals such as lithium and the like, alkaline-earth metals such as calcium and the like, and elemental metals such as aluminum, titanium, manganese, silver, lead, chromium, and the like. Alloys including combinations of these elemental metals may be used. For example, magnesium-silver, aluminum-lithium, aluminum-magnesium, and the like can be used. Also, metal oxides such as indium tin oxide (ITO) and the like can be used. These electrode materials may be used alone or in combination of two or more. The cathode may include a single layer or multiple layers.

In the organic light-emitting devices according to the present invention, layers containing the organic compounds according to the present invention and layers containing other organic compounds are formed by the method described below. In general, thin films are formed by a vacuum evaporation method, an ionized evaporation method, sputtering, plasma, or a known application method (e.g., spin coating, dipping, casting, a LB method, an ink jet method, or the like) using an appropriate solvent solution. When layers are formed by the vacuum evaporation method, the solution application method, or the like, crystallization little occurs, and excellent temporal stability is exhibited. When films are formed by the application method, the films can be formed by combining an appropriate binder resin with the organic compounds.

Examples of the binder resin include, but are not limited to, polyvinyl carbazole resins, polycarbonate resins, polyester resins, ABS resins, acrylic resins, polyimide resins, phenol resins, epoxy resins, silicone resins, urea resins, and the like. These binder resins may be used alone as a homopolymer or a copolymer or as a mixture or two or more. Further, known additives such as a plasticizer, an antioxidant, an ultraviolet absorber, and the like may be added according to demand.

(Use of Organic Light-Emitting Device)

The organic light-emitting device according to the present invention can be used for a display device and an illuminating device. Other uses include an exposure light source of an electrophotographic image forming apparatus, a backlight of a liquid crystal display device, and the like.

The display device includes the organic light-emitting device according to the present invention provided in a display portion. The display portion includes a pixel having the organic light-emitting device according to the present invention. The display device can be used as an image display device of PC or the like.

The display device may be used in a display portion of an imaging apparatus such as a digital camera, a digital video camera, or the like. The imaging apparatus includes the display portion and an imaging portion having an imaging optical system for taking images.

Next, the display device using the organic light-emitting device according to the present invention is described.

FIG. 1 is a schematic sectional view showing the organic light-emitting device according to the present invention and TFT connected to the organic light-emitting device in order to drive the organic light-emitting device. Details of a structure are described below.

A display device 3 shown in FIG. 3 includes a substrate 31 of glass or the like and a moisture-proofing film 32 provided on the substrate 31 in order to protect TFT or an organic compound layer. Reference numeral 33 denotes a gate electrode composed of a metal such as Cr or the like. Reference numeral 34 denotes a gate insulating film and reference numeral 35 denotes a semiconductor layer.

A TFT device 38 includes the semiconductor layer 35, a drain electrode 36, and a source electrode 37. In addition, an insulating film 39 is provided on the TFT device 38. An anode 311 of the organic light-emitting device is connected to the source electrode 37 through a contact hole (through hole) 310.

In this FIGURE, a multilayer organic compound layer 312 is shown as a single layer. Further, a first protective layer 314 and a second protective layer 315 are provided on a cathode 313 in order to suppress deterioration of the organic light-emitting device.

The light-emission luminance of the organic light-emitting device is controlled by the TFT device. A plurality of organic light-emitting devices are provided in a plane so that an image can be displayed by the light-emission luminance of each organic light-emitting device.

By driving the display device using the organic light-emitting devices of the present invention, display can be made with good image quality and long-term stability.

EXAMPLES

Examples are described below. The present invention is not limited to these examples.

Example 1

Synthesis of Exemplified Compound A8

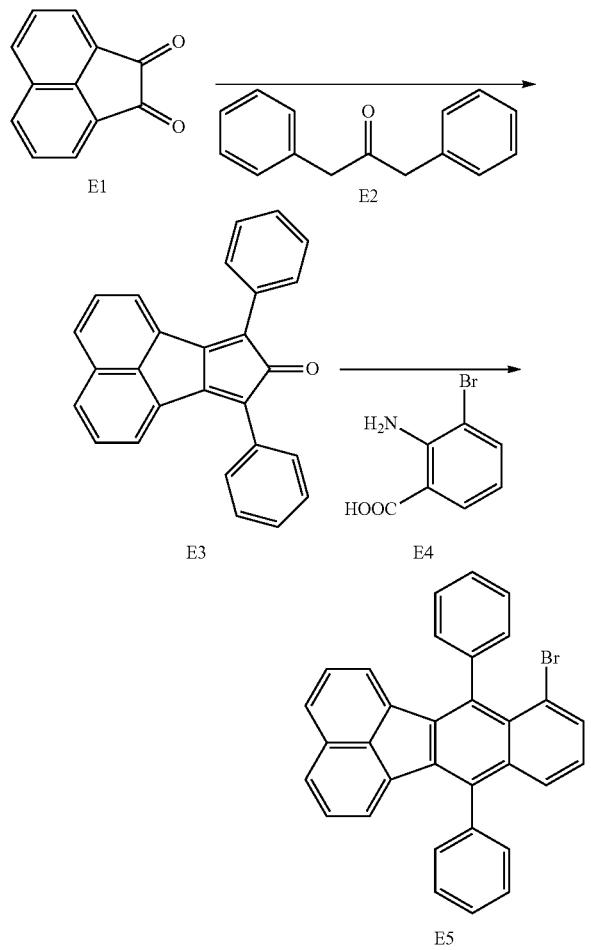

First, 9.1 g (50 mmol) of E1 and 10.5 g (50 mmol) of E2 were placed in 200 ml of ethanol and heated to 60° C., and then 20 ml of a 5M aqueous sodium hydroxide solution was added dropwise. After the addition, the resultant mixture was heated to 80° C., stirred for 2 hours, and then cooled. Then, the resultant precipitates were filtered off, washed with water and ethanol, and then dried by heating at 80° C. under reduced pressure to prepare 15.6 g (yield: 88%) of dark green solid E3. Next, 3.56 g (10 mmol) of E3 and 2.59 g (12 mmol) of E4 were placed in 50 ml of toluene and heated to 80° C., and then 1.40 g (12 mmol) of isoamyl nitrite was slowly added dropwise, followed by stirring at 110° C. for 3 hours. After cooling, the mixture was washed two times with 100 ml of water each time. The resultant organic layer was washed with saturated saline and dried with magnesium sulfate. Then, the solution was filtered, and the filtrate was concentrated to obtain a brownish-red liquid. The liquid was purified by column chromatography (toluene/heptane=2:3) and then recrystallized with chloroform/methanol to obtain 3.96 g (yield: 88%) of an isomer mixture as yellow crystal E5.

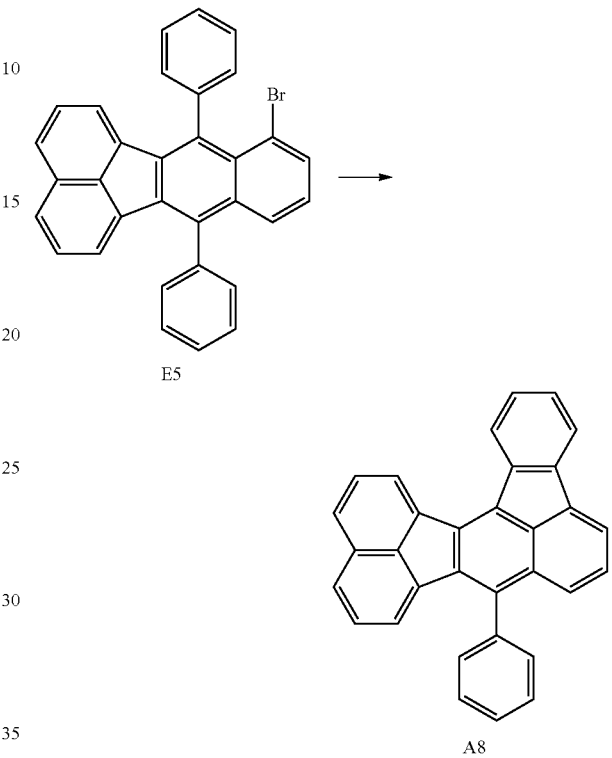

Then, 2.42 g (5 mmol) of E5 was placed in 40 ml of DMF, and 0.25 g (0.5 mmol) of bis(triphenylphosphine)palladium(II) dichloride and 2.28 g (15 mmol) of 1,8-diazabicyclo[5.4.0]undec-7-ene were added to the resultant mixture, followed by heating to 150° C. and stirring for 4 hours. After cooling, 30 ml of methanol was added to the mixture to deposit precipitates which were then filtered off to obtain a yellow solid. The resultant solid was purified by column chromatography (chloroform/heptane=1:4) and then recrystallized with chloroform/methanol two times to obtain 1.35 g (yield: 67%) of exemplified compound A8 as yellow crystals.

Also, the structure of compound A8 was confirmed by NMR measurement.

$^1$H NMR (CDCl$_3$, 500 MHz) σ (ppm): 8.75 (d, 1H, J=7.00 Hz), 8.66 (d, 1H, J=7.55 Hz), 8.05 (d, 1H, J=7.05 Hz), 7.99-7.93 (m, 2H), 7.85-7.79 (m, 2H), 7.66-7.48 (m, 9H), 7.37 (t, 1H, J=7.2 Hz), 6.75 (d, 1H, J=6.95 Hz).

As a result of measurement of photoluminescence of a 1×10$^{-5}$ mol/L toluene solution of exemplified compound A8 at an excitation wavelength of 350 nm using Hitachi F-4500, an emission spectrum having the maximum intensity at 443 nm was observed.

Example 2

Synthesis of Exemplified Compound A20

First, 1.2 g (3 mmol) of A8 obtained in Example 1 and 0.534 g (3 mmol) of N-bromosuccinimide were placed in 50 ml of acetonitrile, and the resultant mixture was stirred at 60°

C. for 8 hours. After cooling, the mixture was concentrated to obtain a solid. The solid was purified by column chromatography (chloroform/heptane=1:4) and recrystallized two times with chloroform/methanol to produce 1.27 g (yield: 88%) of E6. Next, 0.96 g (2 mmol) of E6, 330 mg (2.2 mmol) of 2,6-dimethylphenylboronic acid (E7), 0.05 g of Pd(PPh$_3$)$_4$, 20 ml of toluene, 10 ml of ethanol, and 20 ml of a 2M aqueous sodium carbonate solution were added to a 100 ml eggplant-type flask, followed by stirring in a nitrogen stream at 80° C. for 8 hours. After the completion of reaction, the solution was cooled to room temperature, and the resultant crystals were filtered off and dispersedly washed with water, ethanol, and heptane. The resultant crystals were dissolved in toluene by heating, and the solution was filtered in a hot state and recrystallized with toluene/ethanol. The crystals were dried at 120° C. under vacuum and purified by sublimation to produce 0.73 g (yield: 72%) of exemplified compound A20 as light-yellow crystals.

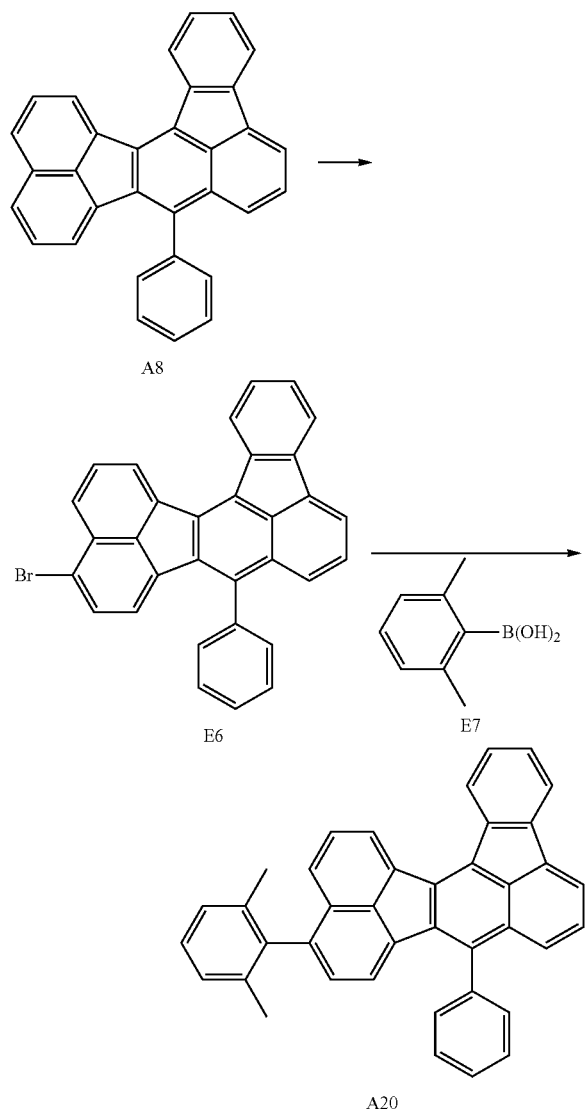

Also, the structure of this compound was confirmed by NMR measurement.

$^1$H NMR (CDCl$_3$, 500 MHz) σ (ppm): 8.75 (d, 1H, J=7.10 Hz), 8.67 (d, 1H, J=7.70 Hz), 8.06 (d, 1H, J=6.60 Hz), 7.99 (d, 1H, J=6.60 Hz), 7.73-7.63 (m, 6H), 7.58-7.48 (m, 4H), 7.42 (d, 1H, J=8.20 Hz), 7.27-7.24 (m, 1H), 7.18-7.13 (m, 3H), 6.81 (d, 1H, J=7.25 Hz), 1.94 (s, 6H).

As a result of measurement of photoluminescence of a 1×10$^{-5}$ mol/L toluene solution of exemplified compound A20 at an excitation wavelength of 350 nm using Hitachi F-4500, an emission spectrum having the maximum intensity at 449 nm was observed.

Example 3

Synthesis of Exemplified Compound A25

E9 was prepared by the same reaction and purification as in Example 1 except that organic compound E4 used in Example 1 was changed to E8.

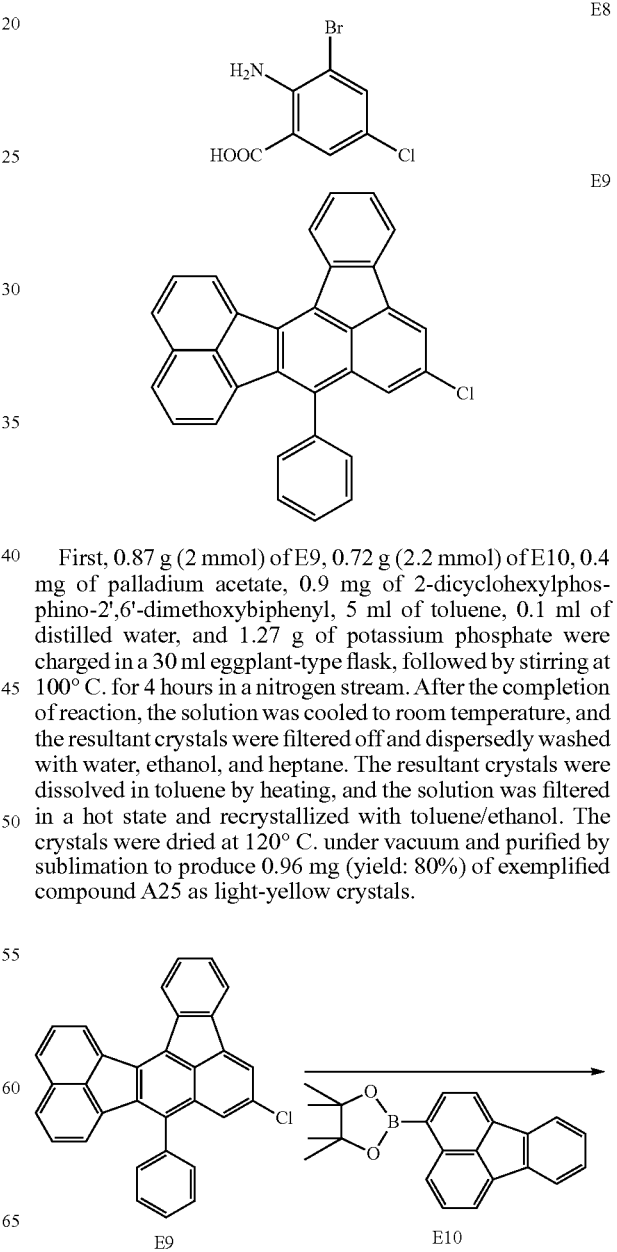

First, 0.87 g (2 mmol) of E9, 0.72 g (2.2 mmol) of E10, 0.4 mg of palladium acetate, 0.9 mg of 2-dicyclohexylphosphino-2',6'-dimethoxybiphenyl, 5 ml of toluene, 0.1 ml of distilled water, and 1.27 g of potassium phosphate were charged in a 30 ml eggplant-type flask, followed by stirring at 100° C. for 4 hours in a nitrogen stream. After the completion of reaction, the solution was cooled to room temperature, and the resultant crystals were filtered off and dispersedly washed with water, ethanol, and heptane. The resultant crystals were dissolved in toluene by heating, and the solution was filtered in a hot state and recrystallized with toluene/ethanol. The crystals were dried at 120° C. under vacuum and purified by sublimation to produce 0.96 mg (yield: 80%) of exemplified compound A25 as light-yellow crystals.

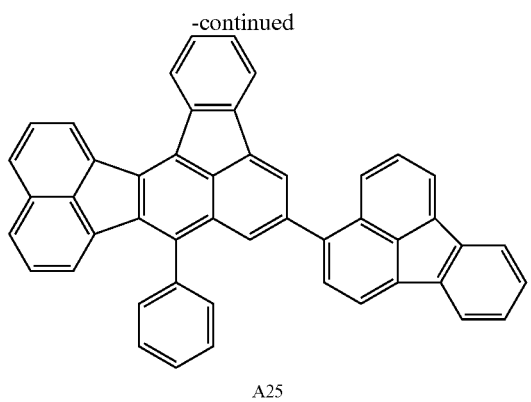

A25

Also, the structure of this compound was confirmed by NMR measurement.

¹H NMR (CDCl₃, 500 MHz) σ (ppm): 8.78 (d, 1H, J=7.05 Hz), 8.71 (d, 1H, J=7.75 Hz), 8.05-7.78 (m, 10H), 7.63-7.48 (m, 8H), 7.41-7.37 (m, 4H), 7.28-7.26 (m, 1H), 6.75 (d, 1H, J=8.50 Hz).

As a result of measurement of photoluminescence of a 1×10⁻⁵ mol/L toluene solution of exemplified compound A25 at an excitation wavelength of 350 nm using Hitachi F-4500, an emission spectrum having the maximum intensity at 450 nm was observed.

Example 4

Synthesis of Exemplified Compound A35

Reaction and purification were performed in the same manner as in Example 3 except that organic compound E10 used in Example 3 was changed to E11.

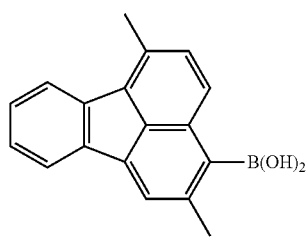

E11

Also, the structure of this compound was confirmed by NMR measurement.

¹H NMR (CDCl₃, 500 MHz) σ (ppm): 8.79 (d, 1H, J=7.10 Hz), 8.71 (d, 1H, J=7.75 Hz), 8.03-7.96 (m, 5H), 7.90-7.80 (m, 3H), 7.62-7.48 (m, 8H), 7.40-7.36 (m, 4H), 7.28-7.26 (m, 1H), 6.75 (d, 1H, J=8.50 Hz), 2.85 (s, 3H), 2.44 (s, 3H).

As a result of measurement of photoluminescence of a 1×10⁻⁵ mol/L toluene solution of exemplified compound A35 at an excitation wavelength of 350 nm using Hitachi F-4500, an emission spectrum having the maximum intensity at 447 nm was observed.

Example 5

Synthesis of Exemplified Compound A23

Reaction and purification were performed in the same manner as in Example 3 except that organic compound E10 used in Example 3 was changed to E12.

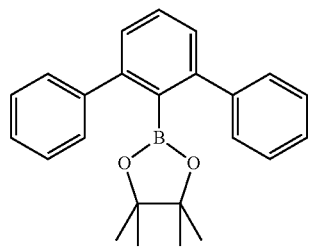

E12

As a result of measurement of photoluminescence of a 1×10⁻⁵ mol/L toluene solution of exemplified compound A23 at an excitation wavelength of 350 nm using Hitachi F-4500, an emission spectrum having the maximum intensity at 449 nm was observed.

Example 6

Synthesis of Exemplified Compound A34

Reaction and purification were performed in the same manner as in Example 3 except that organic compound E10 used in Example 3 was changed to E13.

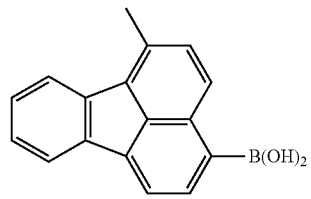

E13

As a result of measurement of photoluminescence of a 1×10⁻⁵ mol/L toluene solution of exemplified compound A34 at an excitation wavelength of 350 nm using Hitachi F-4500, an emission spectrum having the maximum intensity at 450 nm was observed.

Example 7

Synthesis of Exemplified Compound B3

First, 0.96 g (2 mmol) of E6, 0.68 g (2.4 mmol) of E14, 0.38 g (4 mmol) of tert-butoxysodium, and 30 ml of o-xylene were placed in a 100 ml three-necked flask, and the solution was heated to 50° C. Then, a solution of 6 mg of palladium acetate and 27 mg of tert-butylphosphine in 8 ml of o-xylene was slowly added dropwise to the solution, followed by stirring for 6 hours under heating reflux. After the completion of reaction, water was added to the reaction solution, and extraction with toluene was performed. An organic layer was washed with water and dried over magnesium sulfate, and the solvent was removed by distillation under reduced pressure. The residue was purified by silica gel column chromatography (toluene/methanol=9:1) and then recrystallized with toluene. The resultant crystals were dried at 120° C. under vacuum and then purified by sublimation to produce 0.89 g (yield: 65%) of exemplified compound B3 as light-yellow crystals.

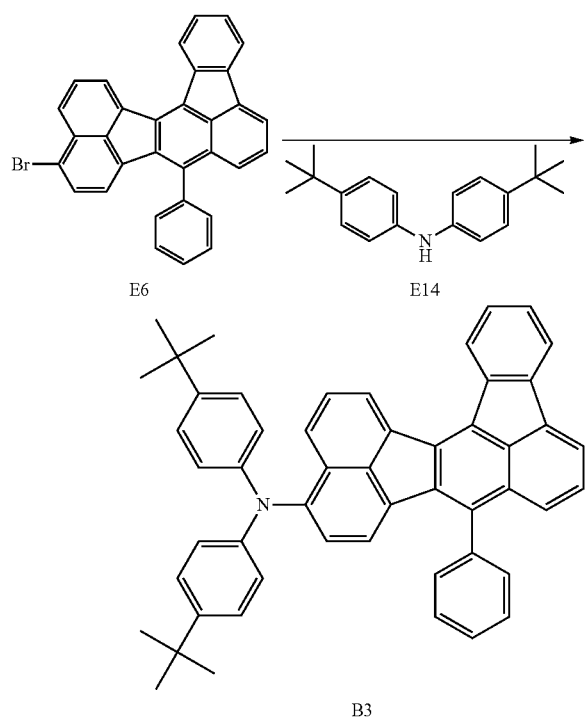

As a result of measurement of photoluminescence of a 1×10⁻⁵ mol/L toluene solution of exemplified compound B3 at an excitation wavelength of 350 nm using Hitachi F-4500, an emission spectrum having the maximum intensity at 495 nm was observed.

Example 8

Synthesis of Exemplified Compound A50

Reaction and purification were performed in the same manner as in Example 1 except that organic compound E2 and organic compound E7 used in Examples 1 and 2 were changed to E15 and E16, respectively.

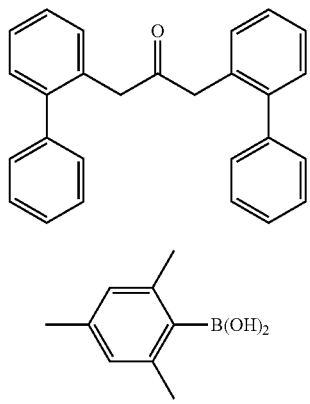

As a result of measurement of photoluminescence of a 1×10⁻⁵ mol/L toluene solution of exemplified compound A50 at an excitation wavelength of 350 nm using Hitachi F-4500, an emission spectrum having the maximum intensity at 449 nm was observed.

Examples 9 to 28

In each of these examples, a device (anode/hole-injection layer/hole-transport layer/light-emitting layer/hole-exciton blocking layer/electron-transport layer/cathode) as a fifth example of multilayer organic light-emitting devices was formed. First, ITO of 100 nm was patterned on a glass substrate. Then, organic layers and electrode layers which are described below were continuously formed on the ITO substrate by resistance-heating vacuum evaporation in a vacuum chamber of $10^{-5}$ Pa so that the opposite electrode area was 3 mm². When two types of guest materials were present, a mixture of structural isomers having different substitution positions at about 1:1 was used.

Hole-transport layer (30 nm) G-1
Light-emitting layer (30 nm) host G-2, guest: exemplified compound (weight ratio 5%)
Hole/exciton blocking layer (10 nm) G-3
Electron-transport layer (30 nm) G-4
Metal electrode layer 1 (1 nm) LiF
Metal electrode layer 2 (100 nm) Al

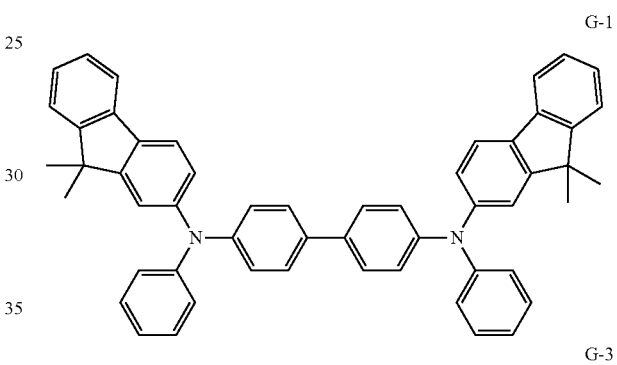

With respect to the characteristics of the EL devices, the current-voltage characteristics were measured with a microammeter 4140B manufactured by Hewlett-Packard Company, and the emission luminance was measured with BM7 manufactured by Topcon Corporation. The emission efficiencies and voltages of Examples 9 to 28 are shown in Table 5.

TABLE 5

| | Guest | G-2 | Emission efficiency (cd/A) | Voltage (V) |
|---|---|---|---|---|
| Example 9 | A8 | H10 | 4.8 | 4.5 |
| Example 10 | A8 | H21 | 4.5 | 4.5 |

TABLE 5-continued

|  | Guest | G-2 | Emission efficiency (cd/A) | Voltage (V) |
|---|---|---|---|---|
| Example 11 | A8 | H22 | 4.0 | 4.2 |
| Example 12 | A16 | H4 | 4.5 | 4.9 |
| Example 13 | A17 | H8 | 3.5 | 4.2 |
| Example 14 | A18 | H2 | 4.9 | 4.5 |
| Example 15 | A20 | H22 | 4.7 | 4.2 |
| Example 16 | A22 | H17 | 4.2 | 4.6 |
| Example 17 | A23 | H21 | 4.9 | 4.6 |
| Example 18 | A25 | H10 | 5.5 | 4.9 |
| Example 19 | A25 | H22 | 5.6 | 4.5 |
| Example 20 | A29 | H5 | 4.5 | 4.8 |
| Example 21 | A30 | H23 | 6.5 | 4.5 |
| Example 22 | A34 | H27 | 5.5 | 4.5 |
| Example 23 | A35 | H10 | 4.8 | 4.2 |
| Example 24 | A38 | H26 | 5.0 | 4.6 |
| Example 25 | A45 | H16 | 4.9 | 4.5 |
| Example 26 | A50 | H4 | 4.6 | 4.9 |
| Example 27 | B3 | H8 | 12.5 | 4.2 |
| Example 28 | B9 | H21 | 4.3 | 5.1 |

Examples 29 to 33

In each of these examples, a multilayer organic light-emitting device of the fifth example was formed. The layer configuration included an anode, a hole-injection layer, a hole-transport layer, a light-emitting layer, an electron-transport layer, an electron-injection layer, and a cathode provided in that order.

An organic light-emitting device having a resonant structure was formed by the following method.

An aluminum alloy (AlNd) was deposited to a thickness of 100 nm by a sputtering method to form a reflective anode on a glass substrate serving as a support member. Further, ITO was deposited to a thickness of 80 nm by a sputtering method to form a transparent anode. Next, a device separating film made of acryl resin was formed to a thickness of 1.5 μm around the anodes, and apertures having a radius of 3 mm were formed. The substrate was ultrasonically washed with acetone and isopropyl alcohol (IPA) in order, washed by boiling with IPA, and then dried. Further, the surface of the substrate was washed with UV/ozone.

Further, organic layers described below were continuously formed by resistance-heating vacuum evaporation in a vacuum chamber of $10^{-5}$ Pa. Then, IZO as a cathode was deposited by a sputtering method to form a transparent electrode having a thickness of 30 nm. After the formation, the substrate was sealed in a nitrogen atmosphere. As a result, an organic light-emitting device was formed.

Hole-injection layer (95 nm) G-11

Hole-transport layer (10 nm) G-12

Light-emitting layer (35 nm) host G-13, guest: exemplified compound (weight ratio 2%)

Electron-transport layer (10 nm) G-14

Electron-injection layer (70 nm) G-15 (weight ratio 80%), Li (weight ratio 20%)

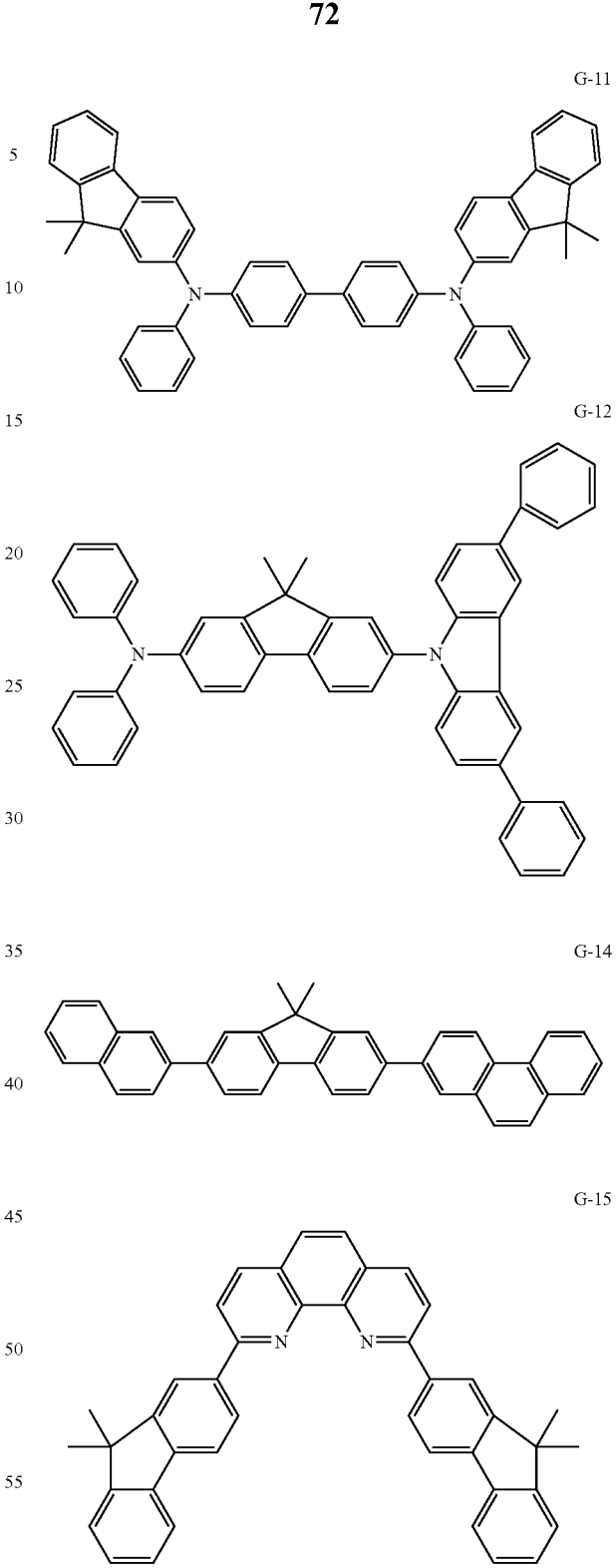

With respect to the characteristics of the EL devices, the current-voltage characteristics were measured with a microammeter 4140B manufactured by Hewlett-Packard Company, and the emission luminance was measured with BM7 manufactured by Topcon Corporation. The emission efficiencies and voltages of Examples 29 to 33 are shown in Table 6.

TABLE 6

|  | Guest | G-13 | Emission efficiency (cd/A) | Voltage (V) |
|---|---|---|---|---|
| Example 29 | A8 | H9 | 3.0 | 4.0 |
| Example 30 | A25 | H10 | 3.1 | 4.2 |
| Example 31 | A30 | H21 | 3.5 | 4.5 |
| Example 32 | A34 | H4 | 3.4 | 4.2 |
| Example 33 | A36 | H18 | 3.1 | 4.3 |

RESULTS AND CONSIDERATION

The organic compounds according to the present invention are novel compounds having high yield and being suitable for blue light emission, and can produce light-emitting devices having good emission characteristics when used for organic light-emitting devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-155667, filed Jun. 30, 2009, which is hereby incorporated by reference herein in its entirety.

The invention claimed is:

1. An organic compound represented by the following general formula (I):

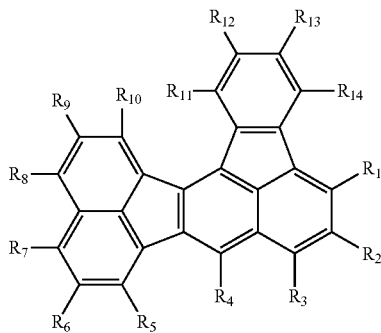

wherein, in general formula (I), $R_1$ to $R_{14}$ are each independently selected from a hydrogen atom, a halogen atom, an alkyl group, an alkoxy group, an amino group, an aryl group, and a heterocyclic group.

2. The organic compound according to claim 1, wherein $R_1$ to $R_{14}$ are each independently selected from a hydrogen atom and an aryl group.

3. An organic light-emitting device comprising an anode, a cathode, and an organic compound layer disposed between the anode and the cathode,
wherein the organic compound layer includes at least one layer containing the organic compound according to claim 1.

4. The organic light-emitting device according to claim 3, wherein the organic compound layer is a light-emitting layer.

5. The organic light-emitting device according to claim 4, wherein blue light is emitted.

6. A display device comprising a plurality of pixels each having the organic light-emitting device according to claim 5 and a thin film transistor which controls the emission luminance of the organic light-emitting device.

7. An imaging device comprising a display portion and an imaging portion,
wherein the display portion includes a plurality of pixels each having the organic light-emitting device according to claim 5 and a thin film transistor which controls the emission luminance of the organic light-emitting device; and
the imaging portion includes an imaging optical system.

8. The organic light-emitting device according to claim 4, wherein the light-emitting layer comprises a compound selected from a group consisting of a fluorene derivative, a naphthalene derivative, an anthracene derivative, a pyrene derivative, a carbazole derivative, a quinoxaline derivative, a quinoline derivative, tris(8-quinolinolate) aluminum, an organic zinc complex, a triphenylamine derivative, a poly(fluorene) derivative, and a poly(phenylene) derivative.

9. An illuminating device comprising the organic light-emitting device according to claim 3.

10. An electrophotographic image forming apparatus comprising an exposure light source,
the exposure light source comprising the organic light-emitting device according to claim 3.

* * * * *